(12) United States Patent
Kincaid et al.

(10) Patent No.: US 12,378,240 B2
(45) Date of Patent: Aug. 5, 2025

(54) NAPHTHYRIDINONE-ANILINE COMPOUNDS FOR TREATMENT OF DERMAL DISORDERS

(71) Applicant: NFlection Therapeutics, Inc., Boston, MA (US)

(72) Inventors: John Kincaid, Boston, MA (US); Matthew Duncton, Boston, MA (US)

(73) Assignee: NFLECTION THERAPEUTICS, INC., Boston, MA (US)

( * ) Notice: Subject to any disclaimer, the term of this patent is extended or adjusted under 35 U.S.C. 154(b) by 785 days.

(21) Appl. No.: 17/294,804

(22) PCT Filed: Nov. 20, 2019

(86) PCT No.: PCT/US2019/000070
§ 371 (c)(1),
(2) Date: May 18, 2021

(87) PCT Pub. No.: WO2020/106308
PCT Pub. Date: May 28, 2020

(65) Prior Publication Data
US 2022/0144819 A1    May 12, 2022

Related U.S. Application Data

(60) Provisional application No. 62/769,866, filed on Nov. 20, 2018.

(51) Int. Cl.
*C07D 471/04* (2006.01)
*A61K 9/00* (2006.01)
*A61P 17/00* (2006.01)

(52) U.S. Cl.
CPC ......... *C07D 471/04* (2013.01); *A61K 9/0014* (2013.01); *A61P 17/00* (2018.01)

(58) Field of Classification Search
CPC ...... C07D 471/04; A61K 9/0014; A61P 17/00
USPC ...................................................... 514/300
See application file for complete search history.

(56) References Cited

U.S. PATENT DOCUMENTS

| | | | |
|---|---|---|---|
| 4,271,164 A | 6/1981 | Blankley et al. | |
| 5,854,257 A | 12/1998 | Amritage et al. | |
| 6,120,359 A | 11/2000 | Barvian et al. | |
| 6,150,359 A * | 11/2000 | Barvian | C07D 471/04 546/122 |
| 7,803,839 B2 | 9/2010 | Aay et al. | |
| 7,915,250 B2 | 3/2011 | Aay et al. | |
| 8,211,921 B2 | 7/2012 | Blake et al. | |
| 8,252,838 B2 | 8/2012 | Kisak et al. | |
| 8,283,359 B2 | 10/2012 | Hutchings et al. | |
| 8,470,821 B2 | 6/2013 | Ibrahim et al. | |
| 10,988,483 B2 | 4/2021 | Kincaid et al. | |
| 11,161,845 B2 | 11/2021 | Kincaid et al. | |
| 2005/0202001 A1 | 9/2005 | Koo et al. | |
| 2006/0276646 A1 * | 12/2006 | Goldstein | A61P 39/02 546/122 |
| 2009/0082328 A1 | 3/2009 | Li et al. | |
| 2009/0246198 A1 | 10/2009 | Dong et al. | |
| 2010/0075947 A1 | 3/2010 | Aftab et al. | |
| 2010/0256149 A1 | 10/2010 | Goutopoulos et al. | |
| 2012/0082702 A1 | 4/2012 | Delucca et al. | |
| 2013/0345181 A1 | 12/2013 | Bavetsias et al. | |
| 2014/0213598 A1 | 7/2014 | Liu et al. | |
| 2015/0023915 A1 | 1/2015 | Morrison et al. | |
| 2015/0111885 A1 * | 4/2015 | Bennett | C07D 405/06 514/249 |

(Continued)

FOREIGN PATENT DOCUMENTS

| | | |
|---|---|---|
| CN | 105384754 A | 3/2016 |
| WO | WO-1999/001421 | 1/2000 |

(Continued)

OTHER PUBLICATIONS

Papalia et al., Published Aug. 28, 2018, ecancer, vol. 12, pp. 1-5 (Year: 2018).*
Simanshu et al., Published Jun. 29, 2017, Cell, vol. 170, pp. 17-33 (Year: 2017).*
Martin-Liberal et al., Published Mar. 6, 2014, Expert Opinion on Drug Safety, vol. 13, pp. 483-495 (Year: 2014).*
Junttila et al., Published Jan. 2015, Molecular Cancer Therapeutics, vol. 14, pp. 40-47 (Year: 2015).*
Zhao et al., Published May 20, 2014, Nature Reviews Clinical Oncology, vol. 11, pp. 385-400 (Year: 2014).*

(Continued)

*Primary Examiner* — Bahar Craigo
*Assistant Examiner* — Jaret J Crews
(74) *Attorney, Agent, or Firm* — Mintz Levin Cohn Ferris Glovsky and Popeo, P.C.

(57) ABSTRACT

Provided herein are compounds, pharmaceutical compositions comprising the compounds, methods of preparing the compounds, and methods of using the compounds and compositions in treating diseases or disorders in a subject where the subject is in need of an inhibitor of MEK where the compound is according to formula (I): where $R^1$, $R^2$, $R^{2a}$, $R^3$, $R^{3a}$, $R^{3b}$, and subscript n are as described herein.

(I)

24 Claims, 3 Drawing Sheets

(56) References Cited

U.S. PATENT DOCUMENTS

| | | |
|---|---|---|
| 2015/0335644 A1 | 11/2015 | Seykora et al. |
| 2018/0256570 A1 | 9/2018 | Peterson et al. |
| 2019/0224210 A1 | 7/2019 | Barbion et al. |
| 2019/0270734 A1 | 9/2019 | Gasser et al. |
| 2020/0165243 A1 | 5/2020 | Kincaid et al. |
| 2020/0172550 A1 | 6/2020 | Kincaid et al. |
| 2022/0033399 A1 | 2/2022 | Kincaid et al. |

FOREIGN PATENT DOCUMENTS

| | | |
|---|---|---|
| WO | WO-2000/42029 | 7/2000 |
| WO | WO-2003/077914 A1 | 9/2003 |
| WO | WO-2005/121142 A1 | 12/2005 |
| WO | WO-2006045514 A1 | 5/2006 |
| WO | WO-2006/130160 | 12/2006 |
| WO | WO-2007/002433 | 1/2007 |
| WO | WO-2007044515 A1 | 4/2007 |
| WO | WO-2007/088345 | 8/2007 |
| WO | WO-2007123939 A2 | 11/2007 |
| WO | WO-2008/020206 | 2/2008 |
| WO | WO-2008/021389 | 2/2008 |
| WO | WO-2008/024724 | 2/2008 |
| WO | WO-2008/024725 | 2/2008 |
| WO | WO-2008/055236 | 5/2008 |
| WO | WO-2008/067481 | 6/2008 |
| WO | WO-2008079814 A2 | 7/2008 |
| WO | WO-2008/148034 | 12/2008 |
| WO | WO-2009/013462 A1 | 1/2009 |
| WO | WO-2009/082687 | 7/2009 |
| WO | WO-2009/093008 | 7/2009 |
| WO | WO-2009/093009 | 7/2009 |
| WO | WO-2009/093013 | 7/2009 |
| WO | WO-2009/153554 | 12/2009 |
| WO | WO-2011117034 A1 | 9/2011 |
| WO | WO-2012/040636 | 3/2012 |
| WO | WO-2014/179785 | 11/2014 |
| WO | WO-2014/210538 A1 | 12/2014 |
| WO | WO-2018/114092 A1 | 6/2018 |
| WO | WO-2018/213807 A1 | 11/2018 |
| WO | WO-2018/213810 A1 | 11/2018 |
| WO | WO-2019/139970 | 7/2019 |
| WO | WO-2020/101878 A1 | 5/2020 |
| WO | WO-2020/106303 A1 | 5/2020 |
| WO | WO-2020/106304 A1 | 5/2020 |
| WO | WO-2020/106305 A1 | 5/2020 |
| WO | WO-2020/106306 A1 | 5/2020 |
| WO | WO-2020/106307 A1 | 5/2020 |
| WO | WO-2020/106308 A1 | 5/2020 |
| WO | WO-2022/066875 A1 | 3/2022 |
| WO | WO-2022159594 A1 | 7/2022 |
| WO | WO-2022159600 A1 | 7/2022 |

OTHER PUBLICATIONS

Lake et al., Published Jun. 24, 2016, Cellular and Molecular Life Sciences, vol. 73, pp. 4397-4413 (Year: 2016).*

Andrews et al., Published Dec. 10, 2013, Journal of Clinical Oncology, vol. 31, pp. e448-e451 (Year: 2013).*

Chen et al., Published Nov. 2014, JAMA Dermatology, vol. 150, pp. 1209-1212 (Year: 2014).*

Roberts et al., Published Mar. 5, 2018, Journal of Medicinal Chemistry, vol. 61, Issue 6, pp. 2472-2489 (Year: 2018).*

Adams et al., "Design and Synthesis of Orally Available MEK Inhibitors With Potent in Vivo Antitumor Efficacy," Bioorganic & Medicinal Chemistry Letters, 22(7), pp. 2411-2414 (2012).

Akinleye et al., "MEK and the Inhibitors: From Bench to Bedside," Journal of Hematology & Oncology, 6(27), 11 pages (2013).

Aslam, A. et al. Naevus sebaceus: a Mosaic RASopathy. Clinical and Experimental Dermatology, 39 pp. 1-6 (2014).

Hatzivassiliou et al., "Mechanism of MEK inhibition determines efficacy in mutant KRAS-versus BRAF-driven cancers," Nature, 501(7466), pp. 232-236 (2013).

Huang W, et al. PD0325901, a mitogen-activated protein kinase kinase inhibitor, produces ocular toxicity in a rabbit animal model of retinal vein occlusion. J Ocul Pharmacol Ther. Dec. 2009;25(6):519-30.

Farschtschi, S., Mautner, VF., Hollants, S. et al. Keratinocytic epidermal nevus syndrome with Schwann cell proliferation, lipomatous tumour and mosaic KRAS mutation. BMC Med Genet 16, 6 (2015).

International Search Report and Written Opinion for International PCT Application No. PCT/US2018/033544 mailed Aug. 9, 2018 (11 pages).

International Search Report and Written Opinion for International PCT Application No. PCT/US2018/033547, mailed Aug. 9, 2018 (10 pages).

International Search Report and Written Opinion for International PCT Application No. PCT/US2019/000067, mailed Apr. 24, 2020 (11 pages).

International Search Report and Written Opinion for International PCT Application No. PCT/US2019/000069, mailed Mar. 20, 2020 (15 pages).

International Search Report and Written Opinion for International PCT Application No. PCT/US2019/000070, mailed Jan. 30, 2020 (16 pages).

International Search Report and Written Opinion for International PCT Application No. PCT/US2019/000066, mailed Feb. 7, 2020 (16 pages).

International Search Report and Written Opinion for International PCT Application No. PCT/US2019/000068, mailed Feb. 19, 2020 (13 pages).

International Search Report and Written Opinion for International PCT Application No. PCT/US2019/000065, mailed Apr. 24, 2020 (10 pages).

Laing et al., "Fused Thiophene Derivatives as MEK Inhibitors," Bioorganic & Medicinal Chemistry Letters, 22(1), pp. 472-475 (2012).

Minkis K, Geronemus RG, Hale EK. Port wine stain progression: a potential consequence of delayed and inadequate treatment? Lasers Surg Med. Aug. 2009;41(6):423-426.

PubChem-CID; 131273078 Create Date; Oct. 9, 2017. pp. 1-7, p. 2, structure.

PubChem-CID; 69072648 Create Date; Nov. 30, 2012. pp. 1-9, p. 2, structure.

Rice, K. et al., Novel carboxamide-based allosteric MEK Inhibitors: Discovery and Optimization Efforts toward XL518, Medicinal Chemestry Letters 3:416-421, 2012.

Sun,B K. et al, Mosaic activating RAS Mutations in nevus sebaceus and nevus sebaceus syndrome, J Invest Dermatology pp. 824-827. Mar. 2013.

Wallace et al., "Structure-based Design and Synthesis of Pyrrole Derivatives as MEK Inhibitors," Bioorganic & Medicinal Chemistry Letters, 20(14), pp. 4156-4158 (2010).

RN 1347327-80-3 Registry ED Entered STN: Dec. 2, 2011.
RN 1347341-78-9 Registry ED Entered STN: Dec. 2, 2011.
RN 1347421-15-1 Registry ED Entered STN: Dec. 2, 2011.
RN 1348075-68-2 Registry ED Entered STN: Dec. 4, 2011.
RN 1348201-64-8 Registry ED Entered STN: Dec. 4, 2011.
RN 1348347-40-9 Registry ED Entered STN: Dec. 4, 2011.
RN 1348375-35-8 Registry ED Entered STN: Dec. 4, 2011.
RN 1348394-69-3 Registry ED Entered STN: Dec. 4, 2011.
RN 1348492-53-4 Registry ED Entered STN: Dec. 4, 2011.
RN 1348494-88-1 Registry ED Entered STN: Dec. 4, 2011.
RN 1348595-42-5 Registry ED Entered STN: Dec. 4, 2011.
RN 1348618-58-5 Registry ED Entered STN: Dec. 4, 2011.
RN 1348655-12-8 Registry ED Entered STN: Dec. 4, 2011.
RN 1348673-54-0 Registry ED Entered STN: Dec. 4, 2011.
RN 1349147-82-5 Registry ED Entered STN: Dec. 5, 2011.
RN 1349255-80-6 Registry ED Entered STN: Dec. 5, 2011.
RN 1349369-24-9 Registry ED Entered STN: Dec. 6, 2011.
RN 1349383-92-1 Registry ED Entered STN: Dec. 6, 2011.
RN 1349420-35-4 Registry ED Entered STN: Dec. 6, 2011.
RN 1349476-92-1 Registry ED Entered STN: Dec. 6, 2011.
RN 1349510-77-5 Registry ED Entered STN: Dec. 6, 2011.
RN 1349524-53-3 Registry ED Entered STN: Dec. 6, 2011.
RN 1349623-68-2 Registry ED Entered STN: Dec. 6, 2011.

(56) References Cited

OTHER PUBLICATIONS

RN 1349668-73-0 Registry ED Entered STN: Dec. 6, 2011.
RN 1349887-30-4 Registry ED Entered STN: Dec. 6, 2011.
RN 1349985-90-5 Registry ED Entered STN: Dec. 7, 2011.
European Patent Office, Extended European Search Report for EP Application No. 19886663.4, mailed Jun. 29, 2022, 6 pages.
International Search Report and Written Opinion for International application No. PCT/US2021/051710, mailed Feb. 16, 2022, 9 pages.
International Search Report and Written Opinion for International Application No. PCT/US2022/013146, mailed Apr. 8, 2022, 7 pages.
International Search Report and Written Opinion for International Application No. PCT/US2022/013153, mailed Jun. 8, 2022, 12 pages.
Klesse et al., The Use of MEK Inhibitors in Neurofibromatosis Type 1-Associated Tumors and Management of Toxicities, The Oncologist, Apr. 22, 2020, vol. 25, pp. e1109-e1116.
Lu et al., Structure-based design and synthesis of bicylic fused-pyridines as MEK inhibitors, Bioorganic & Medicinal Chemistry Letters, 2014, vol. 24, pp. 2555-2559.
PubChem SID 230153403-SCHEMBL4202810, Feb. 12, 2015, 8 pages.
European Patent Office, Extended European Search Report for EP Application No. 19886174.2, mailed Jul. 20, 2022, 6 pages.
European Patent Office, Partial Supplementary European Search Report for EP Application No. 19887611.2, mailed Jul. 5, 2022, 9 pages.
International Search Report and Written Opinion for International Application No. PCT/US2022/013153, mailed Jun. 8, 2022.

\* cited by examiner

FIG. 1

Scheme 1

FIG. 2

Scheme 2

FIG. 3

Scheme 3

[Reaction scheme showing synthesis of compound (Ib)]

Step 1: Compound (101) with F, Br substituents and R³ᵃ, R³ᵇ on pyridine + ClC(O)OMe, nBuLi, N(iPr)₂H, THF → Compound (102) (methyl ester added)

Step 2: (102) + (103) [(Z)-2-ethoxyvinyl pinacol boronate], PdXPhos G2, Cs₂CO₃, THF/H₂O → Compound (104)

Step 3: (104) + R¹NH₂ or protected R¹NH₂, HCl, Et₃N, dioxane → Compound (109) (imine intermediate)

Step 4: (109) + NaCNBH₃, dioxane → Compound (110) (bicyclic lactam with F)

Step 5: (110) 1) Aniline, LiHMDS, THF; 2) optional deprotection → Compound (Ib)

when R¹ is HOC(O)-C₁-C₆ alkyl, or
R¹ is -OR⁴ wherein R⁴ is HOC(O)-C₁-C₆ alkyl
→ Compound (Ib)

R¹ is R⁵C(O)-C₁-C₆ alkyl or -OR⁴;
wherein R⁴ is R⁵C(O)-C₁-C₆ alkyl

NAPHTHYRIDINONE-ANILINE COMPOUNDS FOR TREATMENT OF DERMAL DISORDERS

CROSS-REFERENCES TO RELATED APPLICATIONS

This application is a U.S. National Phase Application of PCT International Application No. PCT/US2019/000070, filed Nov. 20, 2019, which claims priority to U.S. Provisional Application No. 62/769,866, filed Nov. 20, 2018, the contents of which are incorporated herein in their entirety and for all purposes.

BACKGROUND OF THE INVENTION

Neurofibromatosis type 1 (NF1) occurs in approximately 1:3,500 births, and is one of the most common autosomal dominant single-gene disorders affecting neurological function in humans. Clinically, NF1 disease is characterized by the presence of benign peripheral nerve tumors, called neurofibromas, involving Schwann cells with biallelic mutations in the NF1 gene, as well as other tumor and non-tumor manifestations. See Jousma et al. Pediatr. Blood Cancer 62: 1709-1716, 2015. NF1 is associated with several dermal disorders, including dermal neurofibromas; plexiform neurofibromas; café au lait spots; and axillary and inguinal freckling. Dermal neurofibromas occur in over 95% of NF1 patients, can appear anywhere on the body, causing itching, irritation, infection, physical pain, and disfigurement. Moreover, dermal neurofibromas are associated with social isolation and anxiety.

NF1 is caused by one or more germ line mutations in NF1, a gene that inactivates the RAS pathway. Because the NF1 gene encodes a Ras-GAP protein, NF1 loss results in high Ras-GTP. Therefore, NF1 research has focused intensively on testing inhibitors in the Ras signaling pathway, including the Ras-MAPK cascade. See Jousma et al. Pediatr. Blood Cancer 62: 1709-1716, 2015. Four distinct MAPK cascades have been identified and named according to their MAPK module. See Akinleye et al. Journal of Hematology & Oncology 6:27, 2013. MEK proteins belong to a family of enzymes that lie upstream to their specific MAPK targets in each of the four MAP kinase signaling pathways. Two of these MEK proteins, MEK1 and MEK2, are closely related and participate in this signaling pathway cascade. Inhibitors of MEK1 and MEK2 have been shown to effectively inhibit MEK signaling downstream of Ras, and thus provide a strong rationale for targeting MEK in the treatment of NF1. See Rice et al. Medicinal Chemistry Letters 3:416-421, 2012.

Currently available MEK inhibitors are designed to have oral bioavailability for systemic delivery, and are associated with significant side effects including decreased left ventricular ejection fraction, elevated creatine phosphokinase, pneumonitis, renal failure, diarrhea, infection, uticaria, and maculo-papular rash, all of which are dose limiting or require permanent discontinuation. Moreover, clinical trials have shown side effects with prolonged high-dose administration of MEK inhibitors. See Huang et al. J. Ocul. Pharmacol. Ther. 25:519-530, 2009. For example, PD0325901, a MEK inhibitor currently in clinical trials, has exhibited neurological side effects associated with ataxia, confusion, and syncope. In addition, a number of other side effects have been observed with systemic exposure to MEK inhibitors including: acneiform rash, CPK elevation, nausea, vomiting, diarrhea, abdominal pain, and fatigue. Thus, there is a need for therapies that inhibit MEK to treat NF1 associated dermal neurofibromas, which limit these serious side effects.

BRIEF SUMMARY OF THE INVENTION

In one aspect, provided herein is a compound of formula (I):

or a stereoisomer, mixture of stereoisomers, and/or a pharmaceutically acceptable salt thereof,
wherein:
  subscript n is an integer from 0 to 2;
  bond "a" is a single or double bond;
  $R^1$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl)amino-$C_1$-$C_6$ alkyl, heterocycloalkyl, heterocycloalkyl-$C_1$-$C_6$ alkyl, $R^5$—C(O)—$C_1$-$C_6$ alkyl, or —$OR^4$, wherein each of the $C_3$-$C_8$ cycloalkyl and heterocycloalkyl groups is unsubstituted or substituted with one to six $R^6$;
  $R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
  $R^{2a}$ is halo or $C_1$-$C_6$ alkyl;
  each $R^3$ is independently halo or $C_1$-$C_6$ alkyl;
  $R^{3a}$ and $R^{3b}$ are each independently hydrogen, halo, $C_1$-$C_6$ alkyl, $C_2$-$C_6$ alkenyl, or $C_2$-$C_6$ alkynyl;
  $R^4$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl)amino-$C_1$-$C_6$ alkyl, heterocycloalkyl, heterocycloalkyl-$C_1$-$C_6$ alkyl, or $R^5$—C(O)—$C_1$-$C_6$ alkyl, wherein each of the $C_3$-$C_8$ cycloalkyl and heterocycloalkyl groups is unsubstituted or substituted with one to six $R^6$;
  $R^5$ is hydroxy, $C_1$-$C_6$ alkoxy, amino, $C_1$-$C_6$ alkylamino, di-($C_1$-$C_6$ alkyl)amino, hydroxyamino, or N—$C_1$-$C_6$ alkyl hydroxyamino; and
  each $R^6$ is independently halo, hydroxy, oxo, $C_1$-$C_6$ alkyl, $C_3$-$C_8$ cycloalkyl, $C_1$-$C_6$ alkoxy, $C_1$-$C_6$-hydroxyalkyl, $C_1$-$C_6$ haloalkyl, amino, $C_1$-$C_6$ alkylamino, di-($C_1$-$C_6$ alkyl)amino, amino-$C_1$-$C_6$ alkyl, $C_1$-$C_6$ alkylamino-$C_1$-$C_6$ alkyl, or di-($C_1$-$C_6$ alkyl) amino-$C_1$-$C_6$ alkyl.

In a second aspect, provided herein is a pharmaceutical composition including the compound of formula (I) and a pharmaceutically acceptable carrier.

In a third aspect, provided herein is a method of treating a MEK-inhibitor responsive disorder, a MEK-inhibitor responsive dermal disorder, a MEK-mediated disorder or disease, or a MEK-mediated dermal disorder, the method including administering a therapeutically effective amount of a compound of formula (I) or a composition of the compound of formula (I), thereby treating the disorder or disease.

BRIEF DESCRIPTION OF THE DRAWINGS

FIG. 1 shows synthesis Scheme 1 for the preparation of a compound of formula (Ia).

FIG. 2 shows synthesis Scheme 2 for the preparation of a compound of formula (Ia).

FIG. 3 shows synthesis Scheme 3 for the preparation of a compound of formula (Ib).

DETAILED DESCRIPTION OF THE INVENTION

I. General

Provided herein are compounds of formula (I), pharmaceutical compositions including the compounds of formula (I), and methods of using these compounds or compositions in the treatment of a MEK-inhibitor responsive disorder or disease, a MEK-inhibitor responsive dermal disorder or disease, a MEK-mediated disorder or disease, or a MEK-mediated dermal disorder or disease.

II. Definition

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

"Alkyl" refers to a straight or branched, saturated, aliphatic radical having the number of carbon atoms indicated (i.e., $C_1$-$C_6$ means one to six carbons). Alkyl can include any number of carbons, such as $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

"Alkylene" refers to a straight or branched, saturated, aliphatic radical having the number of carbon atoms indicated (i.e., $C_1$-$C_6$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkenyl" refers to a straight chain or branched hydrocarbon having at least 2 carbon atoms and at least one double bond and having the number of carbon atom indicated (i.e., $C_2$-$C_6$ means to two to six carbons). Alkenyl can include any number of carbons, such as $C_2$, $C_2$-$C_3$, $C_2$-$C_4$, $C_2$-$C_5$, $C_2$-$C_6$, $C_2$-$C_7$, $C_2$-$C_8$, $C_2$-$C_9$, $C_2$-$C_{10}$, $C_3$, $C_3$-$C_4$, $C_3$-$C_5$, $C_3$-$C_6$, $C_4$, $C_4$-$C_5$, $C_4$-$C_5$, $C_5$, $C_5$-$C_6$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkynyl" refers to either a straight chain or branched hydrocarbon having at least 2 carbon atoms and at least one triple bond and having the number of carbon atom indicated (i.e., $C_2$-$C_6$ means to two to six carbons). Alkynyl can include any number of carbons, such as $C_2$, $C_2$-$C_3$, $C_2$-$C_4$, $C_2$-$C_5$, $C_2$-$C_6$, $C_2$-$C_7$, $C_2$-$C_8$, $C_2$-$C_9$, $C_2$-$C_{10}$, $C_3$, $C_3$-$C_4$, $C_3$-$C_5$, $C_3$-$C_6$, $C_4$, $C_4$-$C_5$, $C_4$-$C_6$, $C_5$, $C_5$-$C_6$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_3$-$C_6$, $C_4$-$C_6$, $C_5$-$C_6$, $C_3$-$C_8$, $C_4$-$C_8$, $C_5$-$C_8$, $C_6$-$C_8$, $C_3$-$C_9$, $C_3$-$C_{10}$, $C_3$-$C_{11}$, and $C_3$-$C_{12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_3$-$C_8$ cycloalkyl, exemplary groups include, but are not limited to cyclopropyl, cyclobutyl, cyclopentyl, cyclohexyl, cycloheptyl and cyclooctyl.

"Cycloalkylalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. The alkyl component can include any number of carbons, such as $C_1$-$C_6$, $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. The cycloalkyl component is as defined above. Exemplary cycloalkyl-alkyl groups include, but are not limited to, cyclopropylmethyl, cyclobutylmethyl, cyclopentylmethyl and cyclohexylmethyl.

"Alkoxy" refers to an alkyl group having an oxygen atom that connects the alkyl group to the point of attachment: alkyl-O—. Alkoxy groups can have any suitable number of carbon atoms, such as $C_1$-$C_6$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Hydroxyalkyl" refers to an alkyl group, as defined above, where at least one of the hydrogen atoms is replaced with a hydroxy group. As for the alkyl group, a hydroxyalkyl group can have any suitable number of carbon atoms, such as $C_1$-$C_6$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_1$-$C_2$, $C_1$-$C_3$, $C_1$-$C_4$, $C_1$-$C_5$, $C_1$-$C_6$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. The alkoxy component is as defined above. Examples of the alkoxy-alkyl group include, but are not limited to, 2-ethoxyethyl and methoxymethyl.

"Halogen" or "halo" refers to fluoro, chloro, bromo, or iodo.

"Haloalkyl" refers to alkyl, as defined above, where some or all of the hydrogen atoms are replaced with halogen atoms. As for alkyl group, haloalkyl groups can have any suitable number of carbon atoms, such as $C_1$-$C_6$. For example, haloalkyl includes trifluoromethyl, fluoromethyl, 2,2,2-trifluoroethyl, etc. In some instances, the term "perfluoro" can be used to define a compound or radical where all the hydrogens are replaced with fluorine. For example, perfluoromethyl refers to 1,1,1-trifluoromethyl.

"Amino" as used herein, and unless otherwise specified, refers to —$NH_2$.

"Alkylamino" as used herein, and unless otherwise specified, refers to an —NHR radical where R is alkyl as defined herein, or an N-oxide derivative thereof. In some embodiments, alkylamino is $C_1$-$C_6$ alkylamino. In some embodiments, $C_1$-$C_6$ alkylamino is methylamino, ethylamino, n-, iso-propylamino, n-, iso-, tert-butylamino, or methylamino-N-oxide, and the like.

"Dialkylamino" as used herein, and unless otherwise specified, refers to an —NR'R radical where R and R' are independently alkyl as defined herein, or an N-oxide derivative thereof. In some embodiments, dialkylamino is di-($C_1$-$C_6$ alkyl)amino. In some embodiments, di-($C_1$-$C_6$ alkyl) amino is dimethylamino, methyl-ethylamino, diethylamino, or dimethylamino-N-oxide, and the like.

"Aminoalkyl" as used herein, unless otherwise specified, refers to an alkyl group substituted with one or two $NH_2$. In some embodiments, aminoalkyl is amino-$C_1$-$C_6$ alkyl.

"Alkylaminoalkyl" as used herein, unless otherwise specified, refers to an alkyl group substituted with one or two —NH(alkyl) groups. In some embodiments, alkylaminoalkyl is $C_1$-$C_6$ alkylamino-$C_1$-$C_6$ alkyl.

"Dialkylaminoalkyl" as used herein, unless otherwise specified, refers to an alkyl group substituted with one or two —N(alkyl)$_2$ groups. In some embodiments, dialkylaminoalkyl is di-($C_1$-$C_6$ alkyl)amino-$C_1$-$C_6$ alkyl.

"Hydroxyamino" as used herein, unless otherwise specified, refers to —NHOH.

"N-alkylhydroxyamino" as used herein, unless otherwise specified, refers to the amine hydrogen of —NHOH is substituted with alkyl as defined herein. In some embodiments, N-alkyl hydroxyamino is N—$C_1$-$C_6$ alkyl-hydroxyamino. In some embodiments, N—$C_1$-$C_6$ alkyl-hydroxyamino is N-methylhydroxyamino, N-ethylhydroxyamino, N-(n-, iso-propyl)hydroxyamino, or N-(n-, iso-, tert-butyl)hydroxyamino, and the like.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridinyl, azetidinyl, pyrrolidinyl, piperidinyl, azepanyl, azocanyl, quinuclidinyl, pyrazolidinyl, imidazolidinyl, piperazinyl (1,2-, 1,3- and 1,4-isomers), oxiranyl, oxetanyl, tetrahydrofuranyl, oxanyl (tetrahydropyranyl), oxepanyl, thiiranyl, thietanyl, thiolanyl (tetrahydrothiophenyl), thianyl (tetrahydrothiopyranyl), oxazolidinyl, isoxazolidinyl, thiazolidinyl, isothiazolidinyl, dioxolanyl, dithiolanyl, morpholinyl, thiomorpholinyl, dioxanyl, or dithianyl. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_1$-$C_6$ alkyl or oxo (=O), among many others.

The heterocycloalkyl groups can be linked via any position on the ring. For example, aziridinyl can be 1- or 2-aziridinyl, azetidinyl can be 1- or 2-azetidinyl, pyrrolidinyl can be 1-, 2- or 3-pyrrolidinyl, piperidinyl can be 1-, 2-, 3- or 4-piperidinyl, pyrazolidinyl can be 1-, 2-, 3-, or 4-pyrazolidinyl, imidazolidinyl can be 1-, 2-, 3- or 4-imidazolidinyl, piperazinyl can be 1-, 2-, 3- or 4-piperazinyl, tetrahydrofuranyl can be 1- or 2-tetrahydrofuranyl, oxazolidinyl can be 2-, 3-, 4- or 5-oxazolidinyl, isoxazolidinyl can be 2-, 3-, 4- or 5-isoxazolidinyl, thiazolidinyl can be 2-, 3-, 4- or 5-thiazolidinyl, isothiazolidinyl can be 2-, 3-, 4- or 5-isothiazolidinyl, and morpholinyl can be 2-, 3- or 4-morpholinyl.

When heterocycloalkyl includes 3 to 8 ring members and 1 to 3 heteroatoms, representative members include, but are not limited to, pyrrolidinyl, piperidinyl, tetrahydrofuranyl, oxanyl, tetrahydrothiophenyl, thianyl, pyrazolidinyl, imidazolidinyl, piperazinyl, oxazolidinyl, isoxzoalidinyl, thiazolidinyl, isothiazolidinyl, morpholinyl, thiomorpholinyl, dioxanyl and dithianyl. Heterocycloalkyl can also form a ring having 5 to 6 ring members and 1 to 2 heteroatoms, with representative members including, but not limited to, pyrrolidinyl, piperidinyl, tetrahydrofuranyl, tetrahydrothiophenyl, pyrazolidinyl, imidazolidinyl, piperazinyl, oxazolidinyl, isoxazolidinyl, thiazolidinyl, isothiazolidinyl, and morpholinyl.

"Protecting group" refers to a compound that renders a functional group unreactive to a particular set of reaction conditions, but that is then removable in a later synthetic step so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety.

"Salt" refers to acid or base salts of the compounds of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Isomer" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

"Tautomer" refers to one of two or more structural isomers which exist in equilibrium and which are readily converted from one form to another.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound that is complexed to at least one water molecule. The compounds of the present invention can be complexed with from 1 to 10 water molecules.

"Substantially free of" or "substantially in the absence of" stereoisomers with respect to a composition refers to a composition that includes at least 85 or 90% by weight, in some embodiments 95%, 98%, 99% or 100% by weight, of a designated stereoisomer of a compound in the composition. In some embodiments, in the methods and compounds provided herein, the compounds are substantially free of stereoisomers.

"Isolated" with respect to a composition refers to a composition that includes at least 85%, 90%, 95%, 98%, 99% to 100% by weight, of a specified compound, the remainder comprising other chemical species or stereoisomers.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"$IC_{50}$" refers to an amount, concentration or dosage of a particular test compound that achieves a 50% inhibition of a maximal response in an assay that measures such response.

"Inhibition", "inhibits" and "inhibitor" refer to a compound that prohibits or a method of prohibiting, a specific action or function.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The disclosure provides "soft" MEK inhibitors, compositions comprising "soft" MEK inhibitors, and methods of treating and/or preventing a dermal disorder (e.g., a MEK-inhibitor responsive dermal disorder or a MEK mediated dermal disorder, e.g., a dermal rasopathy, e.g., a dermal disorder associated with neurofibromatosis type 1 (NF1), e.g., a dermal neurofibroma, a subdermal neurofibroma, or a superficial plexiform neurofibroma) with MEK inhibitors e.g., "soft" MEK inhibitors. For example, the methods described herein provide administration, e.g., local or non-systemic, e.g., topical, intradermal, or intralesional administration, of MEK inhibitors, e.g., "soft" MEK inhibitors, e.g., "soft" MEK inhibitors described herein, whereby the side effects exhibited with systemic exposure, e.g., known side effects exhibited with MEK inhibitors designed for systemic delivery, are significantly reduced.

In some embodiments, "soft MEK inhibitor" is a compound which inhibits MEK1 and/or 2 and is characterized by a predictable and controllable metabolism/degradation to non-toxic and biologically less active or inactive (i.e. does not inhibit, or inhibits to a lesser degree, MEK1 and/or 2) products after they have achieved their therapeutic role in the skin.

"Hard MEK inhibitor" refers to a MEK inhibitor known in the art. In some embodiments, a hard MEK inhibitor is designed for oral bioavailability. This is necessary to deliver therapeutically effective levels of MEK inhibitor to peripheral lesions with systemic delivery. Hard MEK inhibitor include, for example, PD0325901; PD184161; SMK-17; AS703026 (Pimasertib, MSC1936369); RO-4987655; Selumetinib (AZD6244, ARRY142886); Binimetinib (MEK162, ARRY-162, ARRY-438162); Refametinib; Cobimetinib (GDC-0973, XL518); GDC-0623; AZD8330 (ARRY-424704); CI-1040 (PD184352); PD198306; and PD318088.

While not wishing to be bound by theory, it is believed that soft MEK inhibitors, e.g., such as the "soft" MEK inhibitors described herein, are more metabolically labile than known "hard" MEK inhibitors. Due to their inherent metabolic instability, e.g., for degradation upon reaching the systemic circulation, "soft" MEK inhibitors, e.g., such as the "soft" MEK inhibitors described herein, are dermally active but have low systemic exposure upon local or non-systemic administration, e.g., topical, intradermal, or intralesional administration, because they rapidly degrade upon exposure to plasma or blood or hepatic metabolic enzymes. Unlike "soft" MEK inhibitors, known MEK inhibitors have been historically designed for oral bioavailability, which requires good stability in plasma or blood and good stability to hepatic metabolism necessary to permit systemic delivery at therapeutically effective levels, and are more prone to unwanted side effects and increased toxicity. As a result, "soft" MEK inhibitors, e.g., such as the soft MEK inhibitors described herein, are less systemically toxic.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substitutent group, the compound is substituted with at least one substituent group, wherein each substitutent group is optionally different.

III. Compounds

In one aspect, provided herein is a compound of formula (I):

<chemical structure (I)> or a stereoisomer, mixture of stereoisomers, and/or a pharmaceutically acceptable salt thereof,
wherein:
subscript n is an integer from 0 to 2;
bond "a" is a single or double bond;
$R^1$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl)amino-$C_1$-$C_6$ alkyl, heterocycloalkyl, heterocycloalkyl-$C_1$-$C_6$ alkyl, $R^5$—C(O)—$C_1$-$C_6$ alkyl, or —$OR^4$, wherein each of the $C_3$-$C_8$ cycloalkyl and heterocycloalkyl groups is unsubstituted or substituted with one to six $R^6$;

$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;

$R^{2a}$ is halo or $C_1$-$C_6$ alkyl;

each $R^3$ is independently halo or $C_1$-$C_6$ alkyl;

$R^{3a}$ and $R^{3b}$ are each independently hydrogen, halo, $C_1$-$C_6$ alkyl, $C_2$-$C_6$ alkenyl, or $C_2$-$C_6$ alkynyl;

$R^4$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl)amino-$C_1$-$C_6$ alkyl, heterocycloalkyl, heterocycloalkyl-$C_1$-$C_6$ alkyl, or $R^5$—C(O)—$C_1$-$C_6$ alkyl, wherein each of the $C_3$-$C_8$ cycloalkyl and heterocycloalkyl groups is unsubstituted or substituted with one to six $R^6$;

$R^5$ is hydroxy, $C_1$-$C_6$ alkoxy, amino, $C_1$-$C_6$ alkylamino, di-($C_1$-$C_6$ alkyl)amino, hydroxyamino, or N—$C_1$-$C_6$ alkyl hydroxyamino; and each $R^6$ is independently halo, hydroxy, oxo, $C_1$-$C_6$ alkyl, $C_3$-$C_8$ cycloalkyl, $C_1$-$C_6$ alkoxy, $C_1$-$C_6$-hydroxyalkyl, $C_1$-$C_6$ haloalkyl, amino, $C_1$-$C_6$ alkylamino, di-($C_1$-$C_6$ alkyl)amino, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl.

In some embodiments, the cycloalkyl groups of $R^1$, $R^2$, $R^4$ and $R^6$ are each a saturated monocyclic $C_3$-$C_8$ cycloalkyl. In some embodiments, the $C_3$-$C_8$ cycloalkyl group, as alone or as part of $C_3$-$C_8$ cycloalkyl-$C_1$-$C_6$ alkyl is cyclopropyl or cyclobutyl. In some embodiments, the $C_3$-$C_8$ cycloalkyl group, as alone or as part of $C_3$-$C_8$ cycloalkyl-$C_1$-$C_6$ alkyl, is unsubstituted. In some embodiments, the $C_3$-$C_8$ cycloalkyl group, as alone or as part of $C_3$-$C_8$ cycloalkyl-$C_1$-$C_6$ alkyl, is substituted with one to six $R^6$ and $R^6$ is as defined and described herein.

With reference to $R^6$ as one or more substituents of the $C_3$-$C_8$ cycloalkyl group, in some embodiments, each $R^6$ is independently halo, hydroxy, oxo, $C_1$-$C_6$ alkyl, $C_1$-$C_6$ alkoxy, $C_1$-$C_6$-hydroxyalkyl, $C_1$-$C_6$ haloalkyl, amino, $C_1$-$C_6$ alkylamino, di-($C_1$-$C_6$ alkyl)amino, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl. In some embodiments, each $R^6$ is independently halo, hydroxy, $C_1$-$C_6$ alkyl, $C_1$-$C_6$ alkoxy, $C_1$-$C_6$-hydroxyalkyl, $C_1$-$C_6$ haloalkyl, amino, $C_1$-$C_6$ alkylamino, or di-($C_1$-$C_6$ alkyl)amino. In some embodiments, each $R^6$ is independently halo, hydroxy, $C_1$-$C_6$ alkyl, $C_1$-$C_6$ alkoxy, or amino. In some embodiments, each $R^6$ is independently hydroxy or $C_1$-$C_6$ alkyl. In some embodiments, each $R^6$ is independently hydroxy or amino.

In some embodiments, heterocycloalkyl of $R^1$ and $R^4$ is a 3 to 8 membered heterocycloalkyl having 1 to 3 heteroatoms selected from N, O, and S as ring members. In some embodiments, heterocycloalkyl is a 3 to 6 membered heterocycloalkyl having 1 to 2 heteroatom ring members that are N and/or O. In some embodiments, the heterocycloalkyl group, as alone or as part of heterocycloalkyl-$C_1$-$C_6$ alkyl, is unsubstituted. In some embodiments, the heterocycloalkyl group, as alone or as part of heterocycloalkyl-$C_1$-$C_6$ alkyl, is substituted one to six $R^6$ and $R^6$ is as defined and described herein.

With reference to $R^6$ as one or more substituents of the heterocycloalkyl group, in some embodiments, each $R^6$ is independently halo, hydroxy, oxo, $C_1$-$C_6$ alkyl, $C_1$-$C_6$ alkoxy, $C_1$-$C_6$-hydroxyalkyl, $C_1$-$C_6$ haloalkyl, amino, $C_1$-$C_6$ alkylamino, di-($C_1$-$C_6$ alkyl)amino, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl. In some embodiments, each $R^6$ is independently halo, hydroxy, oxo, $C_1$-$C_6$ alkyl, $C_1$-$C_6$ alkoxy, $C_1$-$C_6$-hydroxyalkyl, $C_1$-$C_6$ haloalkyl, amino, $C_1$-$C_6$ alkylamino, or di-($C_1$-$C_6$ alkyl)amino. In some embodiments, each $R^6$ is independently halo, hydroxy, oxo, $C_1$-$C_6$ alkyl, $C_1$-$C_6$ alkoxy, or amino. In some embodiments, each $R^6$ is independently hydroxy or $C_1$-$C_6$ alkyl. In some embodiments, each $R^6$ is independently hydroxy, oxo, or amino. In some embodiments, each $R^6$ is independently hydroxy or amino.

In some embodiments, each $R^3$ is independently halo or $C_1$-$C_3$ alkyl. In some embodiments, each $R^3$ is independently fluoro, chloro, bromo, iodo, methyl, ethyl, propyl, or isopropyl. In some embodiments, each $R^3$ is methyl.

In some embodiments, $R^{3a}$ and $R^{3b}$ are each independently hydrogen, halo, or $C_1$-$C_6$ alkyl.

In some embodiments, $R^{3a}$ is hydrogen, halo, or $C_1$-$C_6$ alkyl. In some embodiments, $R^{3a}$ is hydrogen. In some embodiments, $R^{3a}$ is halo. In some embodiments, $R^{3a}$ is fluoro, chloro, bromo, or iodo. In some embodiments, $R^{3a}$ is fluoro. In some embodiments, $R^{3a}$ is $C_1$-$C_6$ alkyl. In some embodiments, $R^{3a}$ is methyl, ethyl, propyl, isopropyl, butyl, isobutyl, sec-butyl, tert-butyl, pentyl, isopentyl, or hexyl. In some embodiments, $R^{3a}$ is methyl.

In some embodiments, $R^{3b}$ is hydrogen, halo, or $C_1$-$C_6$ alkyl. In some embodiments, $R^{3b}$ is hydrogen. In some embodiments, $R^{3b}$ is halo. In some embodiments, $R^{3b}$ is fluoro, chloro, bromo, or iodo. In some embodiments, $R^{3b}$ is fluoro. In some embodiments, $R^{3b}$ is $C_1$-$C_6$ alkyl. In some embodiments, $R^{3b}$ is methyl, ethyl, propyl, isopropyl, butyl, isobutyl, sec-butyl, tert-butyl, pentyl, isopentyl, or hexyl. In some embodiments, $R^{3b}$ is methyl.

In some embodiments, $R^{3a}$ and $R^{3b}$ are each hydrogen. In some embodiments, $R^{3a}$ are hydrogen and $R^{3b}$ is halo. In some embodiments, $R^{3a}$ is hydrogen and $R^{3b}$ is fluoro.

In some embodiments, bond "a" is a double bond and the compound is represented by formula (Ia):

(Ia)

wherein $R^1$, $R^2$, $R^{2a}$, $R^3$, $R^{3a}$, $R^{3b}$, and subscript n are as defined herein in any aspect or embodiment described herein.

In some embodiments, bond "a" is a single bond and the compound is represented by formula (Ib):

(Ib)

wherein $R^1$, $R^2$, $R^{2a}$, $R^3$, $R^{3a}$, $R^{3b}$, and subscript n are as defined herein in any aspect or embodiment described herein.

In some embodiments of formula (I), (Ia) or (Ib), subscript n is 0 or 1. In some embodiments, subscript n is 0 and the compound is represented by formula (Ia-1) or (Ib-1):

(Ia-1)

or (Ib-1)

wherein $R^1$, $R^2$, $R^{2a}$, $R^{3a}$, and $R^{3b}$ are as defined herein in any aspect or embodiment described herein.

With reference to any one of formulae (Ia), (Ib), (Ia-1) and (Ib-1), in some embodiments, $R^{3a}$ and $R^{3b}$ are each independently hydrogen, halo, or $C_1$-$C_6$ alkyl. In some embodiments, $R^{3a}$ is hydrogen, halo, or methyl. In some embodiments, $R^{3b}$ is hydrogen, halo, or methyl. In some embodiments, $R^{3a}$ and $R^{3b}$ are each hydrogen. In some embodiments, $R^{3a}$ is hydrogen and $R^{3b}$ is halo. In some embodiments, $R^{3a}$ is hydrogen and $R^{3b}$ is fluoro.

With reference to any one of formulae (I), (Ia), (Ib), (Ia-1), and (Ib-1), in some embodiments, $R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl. In some embodiments, $R^2$ is halo or $C_1$-$C_6$ alkyl. In some embodiments, $R^2$ is halo, —$SCH_3$, —$CH_3$, $C_2$-$C_3$ alkenyl, or $C_2$-$C_3$ alkynyl.

In some embodiments of any one of formulae (I), (Ia), (Ib), (Ia-1), and (Ib-1), $R^2$ is halo. In some embodiments, $R^2$ is fluoro. In some embodiments, $R^2$ is iodo. In some embodiments, $R^2$ is chloro. In some embodiments, $R^2$ is bromo.

In some embodiments of any one of formulae (I), (Ia), (Ib), (Ia-1), and (Ib-1), $R^2$ is $C_1$-$C_6$ alkyl. In some embodiments, $R^2$ is $C_1$-$C_3$ alkyl. In some embodiments, $R^2$ is methyl.

In some embodiments of any one of formulae (I), (Ia), (Ib), (Ia-1), and (Ib-1), $R^2$ is —S—$C_1$-$C_6$ alkyl. In some embodiments, $R^2$ is —S—$C_1$-$C_3$ alkyl. In some embodiments, $R^2$ is —SCH$_3$.

In some embodiments of any one of formulae (I), (Ia), (Ib), (Ia-1), and (Ib-1), $R^2$ is $C_3$-$C_8$ cycloalkyl. In some embodiments, $R^2$ is cyclopropyl.

In some embodiments of any one of formulae (I), (Ia), (Ib), (Ia-1), and (Ib-1), $R^2$ is $C_2$-$C_6$ alkenyl. In some embodiments, $R^2$ is $C_2$-$C_4$ alkenyl. In some embodiments, $R^2$ is vinyl (ethenyl), propenyl, isopropenyl, 1-butenyl, 2-butenyl, isobutenyl, or butadienyl. In some embodiments, $R^2$ is vinyl.

In some embodiments of any one of formulae (I), (Ia), (Ib), (Ia-1), and (Ib-1), $R^2$ is $C_2$-$C_6$ alkynyl. In some embodiments, $R^2$ is $C_2$-$C_3$ alkynyl. In some embodiments, $R^2$ is acetylenyl or propynyl. In some embodiments, $R^2$ is acetylenyl.

In some embodiments of any one of formulae (I), (Ia), (Ib), (Ia-1), and (Ib-1), $R^2$ is halo or $C_1$-$C_3$ alkyl. In some embodiments, $R^{2a}$ is halo or CH$_3$. In some embodiments, $R^{2a}$ is fluoro or CH$_3$. In some embodiments, $R^{2a}$ is iodo or CH$_3$. In some embodiments, $R^{2a}$ is chloro or CH$_3$. In some embodiments, $R^{2a}$ is bromo or CH$_3$.

In some embodiments of any one of formulae (I), (Ia), (Ib), (Ia-1), and (Ib-1), $R^{2a}$ is halo. In some embodiments, $R^{2a}$ is fluoro. In some embodiments, $R^{2a}$ is iodo. In some embodiments, $R^{2a}$ is chloro. In some embodiments, $R^{2a}$ is bromo.

In some embodiments of any one of formulae (I), (Ia), (Ib), (Ia-1), and (Ib-1), $R^{2a}$ is $C_1$-$C_6$ alkyl. In some embodiments, $R^{2a}$ is $C_1$-$C_3$ alkyl. In some embodiments, $R^{2a}$ is CH$_3$.

In some embodiments of any one of formulae (I), (Ia), (Ib), (Ia-1), and (Ib-1), $R^2$ and $R^{2a}$ are each halo. In some embodiments, $R^2$ is halo and $R^{2a}$ is $C_1$-$C_6$ alkyl. In some embodiments, $R^2$ is $C_1$-$C_6$ alkyl and $R^{2a}$ is halo. In some embodiments, $R^2$ is —S—$C_1$-$C_6$ alkyl and $R^{2a}$ is halo. In some embodiments, $R^2$ is —SCH$_3$ and $R^{2a}$ is halo. In some embodiments, $R^2$ is $C_3$-$C_8$ cycloalkyl and $R^{2a}$ is halo. In some embodiments, $R^2$ is cyclopropyl and $R^{2a}$ is halo. In some embodiments, $R^2$ is $C_2$-$C_6$ alkenyl and $R^{2a}$ is halo. In some embodiments, $R^2$ is $C_2$-$C_6$ alkynyl and $R^{2a}$ is halo. In some embodiments, $R^2$ is acetylenyl and $R^{2a}$ is halo. In some embodiments, $R^2$ and $R^{2a}$ are each independently fluoro, chloro, bromo, or iodo. In some embodiments, $R^2$ is iodo and $R^{2a}$ is fluoro. In some embodiments, $R^2$ is fluoro and $R^{2a}$ is iodo. In some embodiments, $R^2$ is halo and $R^{2a}$ is —CH$_3$. In some embodiments, $R^2$ is fluoro and $R^{2a}$ is —CH$_3$. In some embodiments, $R^2$ is iodo and $R^{2a}$ is —CH$_3$. In some embodiments, $R^2$ is —SCH$_3$ and $R^{2a}$ is fluoro. In some embodiments, $R^2$ is acetylenyl and $R^{2a}$ is fluoro.

With reference to any one of formulae (I), (Ia), (Ib), (Ia-1), and (Ib-1), in some embodiments, $R^1$ is hydrogen. In some embodiments, $R^1$ is $C_1$-$C_6$ alkyl. $R^1$ is $C_3$-$C_8$ cycloalkyl unsubstituted or substituted with one to six $R^6$ and $R^6$ is as defined and described herein. In some embodiments, $R^1$ is $C_3$-$C_8$ cycloalkyl unsubstituted or substituted with one to six $R^6$ and each $R^6$ is independently hydroxy or $C_1$-$C_6$ alkyl. In some embodiments, $R^1$ is $C_3$-$C_8$ cycloalkyl-$C_1$-$C_6$ alkyl, wherein the $C_3$-$C_8$ cycloalkyl group is unsubstituted or substituted with one to six $R^6$ and $R^6$ is as defined and described herein. In some embodiments, $R^1$ is $C_3$-$C_8$ cycloalkyl-$C_1$-$C_6$ alkyl, wherein the $C_3$-$C_8$ cycloalkyl group is unsubstituted or substituted with one to six $R^6$ and each $R^6$ is independently hydroxy or $C_1$-$C_6$ alkyl. In some embodiments, $R^1$ is cyclopropyl, cyclobutyl, cyclopropyl-$C_1$-$C_6$ alkyl, or cyclobutyl-$C_1$-$C_6$ alkyl; and each of the cyclopropyl and cyclobutyl groups is unsubstituted or substituted with one to six $R^6$ and $R^6$ is as defined and described herein. In some embodiments, $R^1$ is cyclopropyl, cyclobutyl, cyclopropyl-$C_1$-$C_6$ alkyl, or cyclobutyl-$C_1$-$C_6$ alkyl, each of the cyclopropyl and cyclobutyl groups is unsubstituted or substituted with one to six $R^6$ and each $R^6$ is independently hydroxy or $C_1$-$C_6$ alkyl. In some embodiments, $R^1$ is $C_1$-$C_6$ hydroxyalkyl. In some embodiments, $R^1$ is $C_1$-$C_6$ alkoxy-$C_1$-$C_6$ alkyl. In some embodiments, $R^1$ is amino-$C_1$-$C_6$ alkyl. In some embodiments, $R^1$ is $C_1$-$C_6$ alkylamino-$C_1$-$C_6$ alkyl. In some embodiments, $R^1$ is di-($C_1$-$C_6$ alkyl)amino-$C_1$-$C_6$ alkyl. In some embodiments, $R^1$ is heterocycloalkyl unsubstituted or substituted with one to six $R^6$ and $R^6$ is as defined and described herein. In some embodiments, $R^1$ is heterocycloalkyl unsubstituted or substituted with one to six $R^6$ and each $R^6$ is independently hydroxy or $C_1$-$C_6$ alkyl. In some embodiments, $R^1$ is heterocycloalkyl-$C_1$-$C_6$ alkyl, wherein the heterocycloalkyl group is unsubstituted or substituted with one to six $R^6$ and $R^6$ is as defined and described herein. In some embodiments, $R^1$ is heterocycloalkyl-$C_1$-$C_6$ alkyl, wherein the heterocycloalkyl group is unsubstituted or substituted with one to six $R^6$ and each $R^6$ is independently hydroxy or $C_1$-$C_6$ alkyl. In some embodiments, $R^1$ is oxetanyl-$C_1$-$C_6$ alkyl, azetidinyl-$C_1$-$C_6$ alkyl, pyrrolidinyl-$C_1$-$C_6$ alkyl, piperidinyl-$C_1$-$C_6$ alkyl, or 2,2-dimethyl-1,3-dioxolan-4-yl-$C_1$-$C_6$ alkyl. In some embodiments, $R^1$ is $R^5$—C(O)—$C_1$-$C_6$ alkyl; and $R^5$ is hydroxy, $C_1$-$C_6$ alkoxy, amino, $C_1$-$C_6$ alkylamino, di-($C_1$-$C_6$ alkyl)amino, hydroxyamino, or N—$C_1$-$C_6$ alkyl hydroxyamino. In some embodiments, $R^1$ is $R^5$—C(O)—$C_1$-$C_6$ alkyl; and $R^5$ is hydroxy, $C_1$-$C_6$ alkoxy, amino, or hydroxyamino.

In some embodiments, $R^1$ is selected from the group consisting of hydrogen,

In some embodiments, $R^1$ is $OR^4$. In some embodiments, $R^4$ is hydrogen. In some embodiments, $R^4$ is $C_1$-$C_6$ alkyl. In some embodiments, $R^4$ is $C_3$-$C_8$ cycloalkyl unsubstituted or substituted with one to six $R^6$ and $R^6$ is as defined and described herein. In some embodiments, $R^4$ is $C_3$-$C_8$ cycloalkyl unsubstituted or substituted with one to six $R^6$ and each $R^6$ is independently hydroxy or $C_1$-$C_6$ alkyl. In some embodiments, $R^4$ is $C_3$-$C_8$ cycloalkyl-$C_1$-$C_6$ alkyl, wherein the $C_3$-$C_8$ cycloalkyl group is unsubstituted or substituted with one to six $R^6$ and $R^6$ is as defined and described herein. In some embodiments, $R^4$ is $C_3$-$C_8$ cycloalkyl-$C_1$-$C_6$ alkyl, wherein the $C_3$-$C_8$ cycloalkyl group is unsubstituted or substituted with one to six $R^6$ and each $R^6$ is independently hydroxy or $C_1$-$C_6$ alkyl. In some embodiments, $R^4$ is cyclopropyl, cyclobutyl, cyclopropyl-$C_1$-$C_6$ alkyl, or cyclobutyl-$C_1$-$C_6$ alkyl; and each of the cyclopropyl and cyclobutyl groups is unsubstituted or substituted with one to six $R^6$ and $R^6$ is as defined and described herein. In some embodiments, $R^4$ is cyclopropyl, cyclobutyl, cyclopropyl-$C_1$-$C_6$ alkyl, or cyclobutyl-$C_1$-$C_6$ alkyl, each of the cyclopropyl and cyclobutyl groups is unsubstituted or substituted with one to six $R^6$ and each $R^6$ is independently hydroxy or $C_1$-$C_6$ alkyl. In some embodiments, $R^4$ is $C_1$-$C_6$ hydroxyalkyl. In some embodiments, $R^4$ is $C_1$-$C_6$ alkoxy-$C_1$-$C_6$ alkyl. In some embodiments, $R^4$ is amino-$C_1$-$C_6$ alkyl. In some embodiments, $R^4$ is $C_1$-$C_6$ alkylamino-$C_1$-$C_6$ alkyl. In some embodiments, $R^4$ is di-($C_1$-$C_6$ alkyl)amino-$C_1$-$C_6$ alkyl. In some embodiments, $R^4$ is heterocycloalkyl unsubstituted or substituted with one to six $R^6$ and $R^6$ is as defined and described herein. In some embodiments, $R^4$ is heterocycloalkyl unsubstituted or substituted with one to six $R^6$ and each $R^6$ is independently hydroxy or $C_1$-$C_6$ alkyl. In some embodiments, $R^4$ is heterocycloalkyl-$C_1$-$C_6$ alkyl, wherein the heterocycloalkyl group is unsubstituted or substituted with one to six $R^6$ and $R^6$ is as defined and described herein. In some embodiments, $R^4$ is heterocycloalkyl-$C_1$-$C_6$ alkyl, wherein the heterocycloalkyl group is unsubstituted or substituted with one to six $R^6$ and each $R^6$ is independently hydroxy or $C_1$-$C_6$ alkyl. In some embodiments, $R^4$ is oxetanyl, azetidinyl, pyrrolidinyl, piperidinyl, oxetanyl-$C_1$-$C_6$ alkyl, azetidinyl-$C_1$-$C_6$ alkyl, pyrrolidinyl-$C_1$-$C_6$ alkyl, piperidinyl-$C_1$-$C_6$ alkyl, or 2,2-dimethyl-1,3-dioxolan-4-yl-$C_1$-$C_6$ alkyl. In some embodiments, $R^4$ is $R^5$—C(O)—$C_1$-$C_6$ alkyl; and $R^5$ is hydroxy, $C_1$-$C_6$ alkoxy, amino, $C_1$-$C_6$ alkylamino, di-($C_1$-$C_6$ alkyl)amino, hydroxyamino, or N—$C_1$-$C_6$ alkyl hydroxyamino. In some embodiments, $R^4$ is $R^5$—C(O)—$C_1$-$C_6$ alkyl; and $R^5$ is hydroxy, $C_1$-$C_6$ alkoxy, amino, or hydroxyamino.

In some embodiments, $R^1$ is selected from the group consisting of —OH,

In some embodiments, the compound of formula (I), (Ia), or (Ia-1) is represented by any one of the following formulae:

-continued

-continued wherein $R^2$, $R^{2a}$, $R^{3a}$, and $R^{3b}$ are as defined herein in any aspect or embodiment described herein.

In some embodiments of the above structures having formula (Ia) or (Ia-1), $R^2$ is iodo and $R^{2a}$ is fluoro. In some embodiments of the above structures, $R^2$ is iodo and $R^{2a}$ is methyl. In some embodiments of the above structures, $R^2$ is ethynyl and $R^{2a}$ is fluoro. In some embodiments of the above structures, $R^2$ is ethynyl and $R^{2a}$ is methyl. In some embodiments of the above structures, $R^2$ is —SCH$_3$ and $R^{2a}$ is fluoro. In some embodiments of the above structures, $R^2$ is —SCH$_3$ and $R^{2a}$ is methyl.

In some embodiments of the above structures having formula (Ia) or (Ia-1), $R^{3a}$ and $R^{3b}$ are each hydrogen. In some embodiments of the above structures, $R^{3a}$ is hydrogen and $R^{3b}$ is halo. In some embodiments of the above structures, $R^{3a}$ is hydrogen and $R^{3b}$ is fluoro.

In some embodiments, the compound of formula (I), (Ib), or (Ib-1) is represented by any one of the following formulae:

-continued

-continued wherein R², R²ᵃ, R³ᵃ, and R³ᵇ are as defined herein in any aspect or embodiment described herein.

In some embodiments of the above structures having formula (Ib) or (Ib-1), R² is iodo and R²ᵃ is fluoro. In some embodiments of the above structures, R² is iodo and R²ᵃ is methyl. In some embodiments of the above structures, R² is ethynyl and R²ᵃ is fluoro. In some embodiments of the above structures, R² is ethynyl and R²ᵃ is methyl. In some embodiments of the above structures, R² is —SCH₃ and R²ᵃ is fluoro. In some embodiments of the above structures, R² is —SCH₃ and R²ᵃ is methyl.

In some embodiments of the above structures having formula (Ib) or (Ib-1), R³ᵃ and R³ᵇ are each hydrogen. In some embodiments of the above structures, R³ᵃ is hydrogen and R³ᵇ is halo. In some embodiments of the above structures, R³ᵃ is hydrogen and R³ᵇ is fluoro.

Exemplified compounds of formula (I) are listed in Table 1.

TABLE 1

| Compounds of formula (I) | |
|---|---|
| No. | Structure |
| 1.001 | |
| 1.002 | |

TABLE 1-continued

Compounds of formula (I)

| No. | Structure |
|---|---|
| 1.003 | (structure) |
| 1.004 | (structure) |
| 1.005 | (structure) |
| 1.006 | (structure) |
| 1.007 | (structure) |
| 1.008 | (structure) |
| 1.009 | (structure) |
| 1.010 | (structure) |
| 1.011 | (structure) |
| 1.012 | (structure) |

Additional compounds of formula (I) are listed in Table 2.

TABLE 2

Additional Compounds of formula (I)

| No. | Structure |
| --- | --- |
| 1.013 | 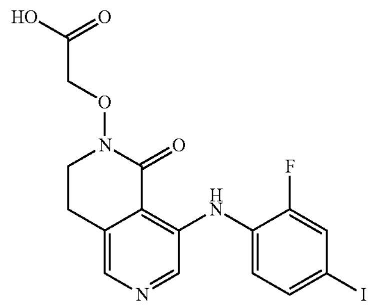 [SMILES: O=C(O)CON1CCc2cncc(Nc3ccc(I)cc3F)c2C1=O] |
| 1.014 | 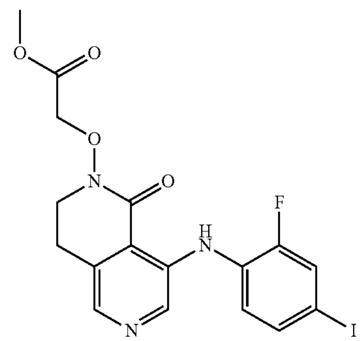 [SMILES: COC(=O)CON1CCc2cncc(Nc3ccc(I)cc3F)c2C1=O] |
| 1.015 | 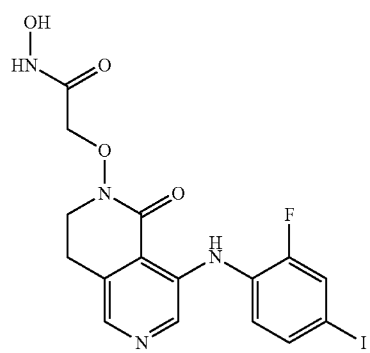 [SMILES: O=C(CON1CCc2cncc(Nc3ccc(I)cc3F)c2C1=O)NO] |
| 1.016 | 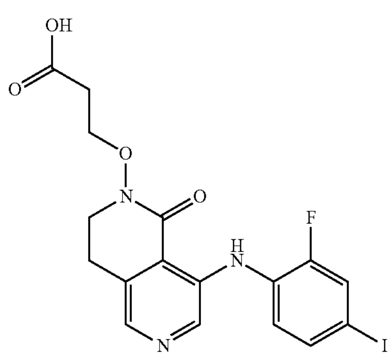 [SMILES: O=C(O)CCON1CCc2cncc(Nc3ccc(I)cc3F)c2C1=O] |
| 1.017 | |
| 1.018 | |
| 1.019 | |
| 1.020 | |

TABLE 2-continued

Additional Compounds of formula (I)

| No. | Structure |
|---|---|
| 1.021 | *(structure)* |
| 1.022 | *(structure)* |
| 1.023 | *(structure)* |

In some embodiments, the compound of formula (I) is selected from the group consisting of:

*(structures shown)*

I, and

*(structure shown)*

I.

Compounds in Other Forms

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Composition

In another aspect, provided herein is a pharmaceutical composition including the compound of formula (I) and a pharmaceutically acceptable carrier.

The compounds provided herein can be formulated into pharmaceutical compositions using methods available in the art and those disclosed herein. Any of the compounds disclosed herein can be provided in the appropriate pharmaceutical composition and be administered by a suitable route of administration.

Administration of the compound described herein to a subject may be local or non-systemic, e.g., topical, intradermal, or intralesional. In some embodiments, the compound can be administered by topical administration. In some embodiments, the compound can be administered by intradermal administration. In some embodiments, the compound can be administered by intralesional administration, e.g., by intralesional injection.

The methods provided herein encompass administering pharmaceutical compositions containing at least one compound as described herein, including a compound of formula (I) if appropriate in a salt form, either used alone or in the form of a combination with one or more compatible and pharmaceutically acceptable carriers, such as diluents or adjuvants, or with another agent for the treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof.

In some embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In some embodiments, the compound provided herein and the second agent are formulated separately. They can be packaged together, or packaged separately, for the convenience of the practitioner of skill in the art.

In clinical practice the active agents provided herein may be administered by any conventional route, in particular topically, intradermally, intralesionally orally, parenterally, rectally or by inhalation (e.g. in the form of aerosols). In some embodiments, the compound provided herein is administered topically, intradermally, or intralesionally. In some embodiments, the compound provided herein is administered topically. In some embodiments, the compound provided herein is administered intradermally. In some embodiments, the compound provided herein is administered intralesionally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in some embodiments, wetting, sweetening or flavoring products.

Use may be made, of compositions for topical administration as lotions, tinctures, creams, emulsions, gels or ointments. In these compositions, the active product is mixed with one or more inert excipients including water, acetone, ethanol, ethylene glycol, propylene glycol, butane 1,3 diol, isopropyl myristate, isopropyl palmitate, mineral oil, and mixtures thereof.

The compositions for parenteral, intralesional, or intradermal administration can be emulsions or sterile solutions. Use may be made, as solvent or vehicle, of propylene glycol, a polyethylene glycol, vegetable oils, in particular olive oil, or injectable organic esters, in some embodiments, ethyl oleate. These compositions can also contain adjuvants, in particular wetting, isotonizing, emulsifying, dispersing and stabilizing agents. Sterilization can be carried out in several ways, in some embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in some embodiments, dextran, mannitol or lactose.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in some embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in some embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In some embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in some embodiments, in purified form, together with a suitable amount of carrier so as to provide the form for proper administration to the subject. The formulation should suit the mode of administration. In some embodiments, the pharmaceutical compositions or single unit dosage forms are sterile and in suitable form for administration to a subject, in some embodiments, an animal subject, such as a mammalian subject, in some embodiments, a human subject.

A pharmaceutical composition is formulated to be compatible with its intended route of administration. In some embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In some embodiments, the route of administration is intradermal, topical, or intralesional administration. In some embodiments, the route of administration is non-systemic administration. In some embodiments, the composition is formulated in accordance with routine procedures as a pharmaceutical composition adapted for intravenous, subcutaneous, intramuscular, oral, intranasal or topical administration to human beings. In some embodiments, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In some embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In some embodiments, a dosage form used in the initial treatment of a MEK-inhibitor responsive disorder or disease, a MEK-inhibitor responsive dermal disorder or disease, a MEK-mediated disorder or disease, or a MEK-mediated dermal disorder or disease may contain larger amounts of one or more of the active ingredients it comprises than a dosage form used in the maintenance treatment of the same disorder or disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in some embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In some embodiments, the oral dosage forms are solid and prepared under anhydrous diseases or disorders with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In some embodiments, excipients suitable for use in oral liquid or aerosol dosage forms include, but are not limited to, water, glycols, oils, alcohols, flavoring agents, preservatives, and coloring agents. In some embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In some embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In some embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In some embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In some embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in some embodiments, a syloid silica gel (AEROSIL 200, manufactured by W.R. Grace Co. of Baltimore, MD), a coagulated aerosol of synthetic silica (marketed by Degussa Co. of Plano, TX), CAB O SIL (a pyrogenic silicon dioxide product sold by Cabot Co. of Boston, MA), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In some embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in some embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the disease or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various diseases or disorders including, but not limited to, pH, temperature, enzymes, water, or other physiological diseases or disorders or compounds.

In some embodiments, the drug may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In some embodiments, polymeric materials can be used. In some embodiments, a controlled release system can be placed in a subject at an appropriate site determined by a practitioner of skill, i.e., thus requiring only a fraction of the systemic dose (see, e.g., Goodson, *Medical Applications of Controlled Release, vol.* 2, pp. 115-138 (1984)). Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In some embodiments, provided are parenteral dosage forms. In some embodiments, parenteral dosage forms can be administered to subjects by various routes including, but not limited to, subcutaneous, intravenous (including bolus injection), intramuscular, and intra-arterial. In some embodiments, parenteral dosage forms can be administered to subjects by various routes including, but not limited to, topical, intradermal, or intralesional. Because their administration typically bypasses subjects' natural defenses against contaminants, parenteral dosage forms are typically, sterile or capable of being sterilized prior to administration to a subject. In some embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In some embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Suitable carriers (e.g., excipients and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical carriers include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. In some embodiments, materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5)

malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In some embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, a doctor will determine the posology which he considers most appropriate according to a preventive or curative treatment and according to the age, weight, stage of the disorder or disease and other factors specific to the subject to be treated. In some embodiments, doses are from about 1 to about 1000 mg per day for an adult, or from about 5 to about 250 mg per day or from about 10 to 50 mg per day for an adult. In some embodiments, doses are from about 5 to about 400 mg per day or 25 to 200 mg per day per adult. In some embodiments, dose rates of from about 50 to about 500 mg per day are also contemplated.

In further aspects, provided are methods of treating a disease or disorder where the subject is in need thereof and/or a MEK-inhibitor responsive disorder or disease, a MEK-inhibitor responsive dermal disorder or disease, a MEK-mediated dermal disorder or disease, or a MEK-mediated dermal disorder or disease in a subject by administering, to a subject in need thereof, a therapeutically or prophylactically effective amount of a compound provided herein, or a pharmaceutically acceptable salt thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In some embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in some embodiments, the dosage administered to a subject is 0.140 mg/kg to 3 mg/kg of the subject's body weight, based on weight of the active compound. In some embodiments, the dosage administered to a subject is between 0.20 mg/kg and 2.00 mg/kg, between 0.30 mg/kg and 1.50 mg/kg, between 1 mg/kg and 100 mg/kg, between 5 mg/kg and 50 mg/kg, between 10 mg/kg and 50 mg/kg, between 20 mg/kg and 50 mg/kg, between 15 mg/kg and 40 mg/kg, between 15 mg/kg and 35 mg/kg, between 15 mg/kg and 30 mg/kg, between 25 mg/kg and 35 mg/kg, between 10 mg/kg and 30 mg/kg, between 10 mg/kg and 20 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg of of the subject's body weight.

In some embodiments, the recommended daily dose range of a composition provided herein for the diseases or disorders described herein lie within the range of from about 0.1 mg to about 1000 mg per day, given as a single once-a-day dose or as divided doses throughout a day. In some embodiments, the daily dose is administered twice daily in equally divided doses. In some embodiments, a daily dose range should be from about 10 mg to about 200 mg per day, in some embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In some embodiments, the dosage administered to the subject may be increased to improve the prophylactic or therapeutic effect of the composition or it may be decreased to reduce one or more side effects that a particular subject is experiencing.

In some embodiments, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In some embodiments, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In some embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In some embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In some embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In some embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In some embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In some embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In some embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In some embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosage may vary within a range depending upon the dosage form employed and the route of administration utilized. For any compound, the therapeutically effective dose can be estimated initially from cell culture assays. A dose may be formulated in animal models to achieve a level in the skin with the lesion, e.g., the dermal neurofibroma, the subdermal neurofibroma, or the superficial plexiform neurofibroma) that includes the $IC_{50}$ (i.e., the concentration of the test compound that achieves a half-maximal inhibition of symptoms) as determined in cell culture. Such information can be used to more accurately determine useful doses in humans. In addition, levels in plasma may be measured, for example, by high performance liquid chromatography, in order to ascertain systemic exposure.

It should also be understood that a specific dosage and treatment regimen for any particular patient will depend upon a variety of factors, including the activity of the specific compound employed, the age, the size of the lesion, number of lesions, general health, sex, diet, time of administration, drug combination, and the judgment of the treating physician and the severity of the particular disease being treated. The amount of a soft MEK inhibitor, e.g., a soft MEK inhibitor described herein, in the composition will also depend upon the particular soft MEK inhibitor in the composition.

In some embodiments, the topical dose is about 0.01 $\mu g/cm^2$, about 0.05 $\mu g/cm^2$, about 0.1 $\mu g/cm^2$, about 0.15 $\mu g/cm^2$, about 0.2 $\mu g/cm^2$, about 0.3 $\mu g/cm^2$, about 0.4 $\mu g/cm^2$, about 0.5 $\mu g/cm^2$, about 0.6 $\mu g/cm^2$, about 0.7 $\mu g/cm^2$, about 0.8 $\mu g/cm^2$, or about 0.9 $\mu g/cm^2$; or is within about 0.01-0.03 $\mu g/cm^2$, about 0.03-0.05 $\mu g/cm^2$, about 0.05-0.1 $\mu g/cm^2$, about 0.1-0.3 $\mu g/cm^2$, about 0.3-0.5 $\mu g/cm^2$, about 0.5-0.8 $\mu g/cm^2$, about 0.8-1.0 $\mu g/cm^2$, about 1-10 $\mu g/cm^2$, about 10-20 $\mu g/cm^2$, about 20-30 $\mu g/cm^2$, about 30-40 $\mu g/cm^2$, about 40-50 $\mu g/cm^2$, about 50-60 $\mu g/cm^2$, about 60-70 $\mu g/cm^2$, about 70-80 $\mu g/cm^2$, about 80-90 $\mu g/cm^2$, about 90-100 $\mu g/cm^2$, about 100-125 $\mu g/cm^2$, about 125-150 $\mu g/cm^2$, about 150-175 $\mu g/cm^2$, about 175-200 $\mu g/cm^2$, about 200-250 $\mu g/cm^2$, about 250-300 $\mu g/cm^2$, about 300-350 $\mu g/cm^2$, about 350-400 $\mu g/cm^2$, about 400-450 $\mu g/cm^2$, about 450-500 $\mu g/cm^2$, about 500-550 $\mu g/cm^2$, about 550-600 $\mu g/cm^2$, about 600-650 $\mu g/cm^2$, about 650-700 $\mu g/cm^2$, about 700-750 $\mu g/cm^2$, about 750-800 $\mu g/cm^2$, about 800-850 $\mu g/cm^2$, about 850-900 $\mu g/cm^2$, about 900-950 $\mu g/cm^2$, or about 950-1000 $\mu g/cm^2$.

In some embodiments, the topical dose is within about 0.5-1.0 $mg/cm^2$, 1.0-1.5 $mg/cm^2$, 1.5-2.0 $mg/cm^2$, 2.5-2.5 $mg/cm^2$, 3.0-3.5 $mg/cm^2$, 3.5-5.0 $mg/cm^2$, 5.0-7.5 $mg/cm^2$, 7.5-10 $mg/cm^2$, 1-10 $mg/cm^2$, about 10-20 $mg/cm^2$, about 20-30 $mg/cm^2$, about 30-40 $mg/cm^2$, about 40-50 $mg/cm^2$, about 50-60 $mg/cm^2$, about 60-70 $mg/cm^2$, about 70-80 $mg/cm^2$, about 80-90 $mg/cm^2$, about 90-100 $mg/cm^2$, about 100-125 $mg/cm^2$, about 125-150 $mg/cm^2$, about 150-175 $mg/cm^2$, about 175-200 $mg/cm^2$, about 200-250 $mg/cm^2$, about 250-300 $mg/cm^2$, about 300-350 $mg/cm^2$, about 350-400 $mg/cm^2$, about 400-450 $mg/cm^2$, about 450-500 $mg/cm^2$, about 500-550 $mg/cm^2$, about 550-600 $mg/cm^2$, about 600-650 $mg/cm^2$, about 650-700 $mg/cm^2$, about 700-750 $mg/cm^2$, about 750-800 $mg/cm^2$, about 800-850 $mg/cm^2$, about 850-900 $mg/cm^2$, about 900-950 $mg/cm^2$, or about 950-1000 $mg/cm^2$.

V. Kits

Also provided are kits for use in methods of treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof; or a MEK-inhibitor responsive disorder or disease, a MEK-inhibitor responsive dermal disorder or disease, a MEK-mediated disorder or disease, or a MEK-mediated dermal disorder or disease. The kits can include a compound or composition provided herein, a second agent or composition, and instructions providing information to a health care provider regarding usage for treating a MEK-inhibitor responsive disorder or disease, a MEK-inhibitor responsive dermal disorder or disease, a MEK-mediated disorder or disease, or a MEK-mediated dermal disorder or disease. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

VI. Methods

In a third aspect, provided herein is a method for treating a disease or disorder where the subject is in need thereof and the disease or disorder is a MEK-inhibitor responsive disorder or disease, a MEK-inhibitor responsive dermal disorder or disease, a MEK-mediated disorder or disease, or a MEK-mediated dermal disorder or disease in a subject. The method includes administering the subject with a therapeutically or prophylactically effective amount of a compound disclosed herein, e.g., a compound of formula (I), and compounds in Tables 1 and 2, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt, solvate, prodrug, phosphate, or active metabolite thereof.

In some embodiments, the method includes administering the subject with a therapeutically effective amount of a compound of formula (I) and compounds in Tables 1 and 2, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt or solvate thereof. In some embodiments, the method includes administering the subject with a therapeutically effective amount of a compound of formula (I) and compounds in Table 1, including a single enantiomer, a mixture of an enantiomeric pair, an individual diastereomer, a mixture of diastereomers, an individual stereoisomer, a mixture of stereoisomers, or a tautomeric form thereof; or a pharmaceutically acceptable salt or solvate thereof.

In some embodiments, the MEK-inhibitor responsive dermal disorder or MEK-mediated dermal disorder is selected from the group consisting of dermal rasopathy, neurofibromatosis type 1, dermal neurofibroma, subdermal neurofibroma, and superficial plexiform neurofibroma.

In some embodiments, the MEK-inhibitor responsive dermal disorder or MEK-mediated dermal disorder is neurofibromatosis type 1.

In some embodiments, administering includes contacting the soft MEK inhibitor with the skin, mucous membranes, vagina, penis, larynx, vulva, cervix, or anus of the subject, by local or non-systemic application, e.g., topical, intradermal, or intralesional application or application by suppository, of the soft MEK inhibitor.

In some embodiments, the tumor associated with neurofibromatosis type 1 (NF1), e.g., a dermal neurofibroma, a subdermal neurofibroma, or a superficial plexiform neurofibroma, is reduced, e.g., the size or the total tumor volume is reduced, by at least about 15% relative to the reference standard (e.g., from about 15% to about 60%), thereby treating the subject. In some embodiments, the reference standard is the size or the total tumor volume in an untreated control, e.g., from the same subject or a different subject.

In some embodiments, the size or total tumor volume of the tumor associated with neurofibromatosis type 1 (NF1), e.g., a dermal neurofibroma, a subdermal neurofibroma, or a superficial plexiform neurofibroma, is reduced by at least about 15%, by at least about 20%, by at least about 25%, by at least about 30%, by at least about 35%, by at least about 40%, by at least about 45%, by at least about 50%, by at least about 55%, by at least about 60% relative to the reference standard. In some embodiments, the reference standard is the size or the total tumor volume in an untreated control, e.g., from the same subject or a different subject.

In some embodiments, the method includes evaluating the subject with magnetic resonance imaging (MRI), or optical imaging, e.g., evaluating the volume of tumors obtained from the subject, e.g., prior to, during and/or after treatment.

Neurofibromatosis type 1 (NF1): In some embodiments, the dermal disorder is associated with NF1. NF1, also known as von Recklinghausen Neurofibromatosis or Peripheral Neurofibromatosis, occurs in approximately 1:3,000 births, and is one of the most prevalent genetic disorders and the most common neurocutaneous disorders. NF1 is caused by a deficiency in neurofibromin, which leads to hyperactivation of various cell-signaling pathways, e.g., Ras and Rho, is associated with several dermal disorders, including dermal neurofibromas (DFs); subdermal neurofibromas; superficial plexiform neurofibromas (PFs); cutaneous neurofibromas (CFs); café au lait spots; and axillary and inguinal freckling. DFs occur in over 95% of NF1 patients. DFs can appear anywhere on the body, with 88% of NF1 patients over 40 years of age having over 100 DFs. DFs can cause both severe physical pain, disfigurement, as well as social anxiety. Facial DFs can create significant social anxiety issues and pain among affected individuals. DFs (also known as cutaneous neurofibromas or discrete neurofibromas) grow from small nerves in the skin or just under the skin and appear as small bumps typically beginning around the time of puberty. Current treatment options for DF are limited to surgical excisin and $CO_2$ laser removal, both of which cause scarring and neither of which is preventative.

Other Dermal Rasopathies: In some embodiments, the dermal disorder is associated with enhanced activation of Ras. In some embodiments, the dermal disorder is selected from: psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots and Multiple lentigines syndrome (formerly called Leopard syndrome).

In some or any embodiments, the disease to be reduced, ameliorated, treated, or prevented is not cancer (e.g. melanoma).

In some embodiments, the disease to be reduced, ameliorated, treated, or prevented is cancer, a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the disease to be reduced, ameliorated, treated, or prevented is cancer. In some embodiments, the disease to be reduced, ameliorated, treated, or prevented is selected from the group consisting of basal cell carcinoma, squamous cell carcinoma, aktinic keratosis, Kaposi's sarcoma, dermal lymphoma, cervical cancer, HPV-related squamous cell carcinoma, and melanoma.

In some embodiments, the disease to be reduced, ameliorated, treated, or prevented is a dermal rasopathy, a dermal disorder associated with neurofibromatosis type 1, a dermal neurofibroma, a subdermal neurofibroma, or a superficial plexiform neurofibroma, psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

In some embodiments, the compounds described herein are used for the reduction of a MEK-inhibitor responsive disorder or disease, a MEK-inhibitor responsive dermal disorder or disease, a MEK-mediated disorder or disease, or a MEK-mediated dermal disorder or disease, where the subject is in need thereof.

In some embodiments, the compounds described herein are used for the amelioration of a MEK-inhibitor responsive disorder or disease, a MEK-inhibitor responsive dermal disorder or disease, a MEK-mediated disorder or disease, or a MEK-mediated dermal disorder or disease, where the subject is in need thereof.

In some embodiments, the compounds described herein are used for prevention of a MEK-inhibitor responsive disorder or disease, a MEK-inhibitor responsive dermal disorder or disease, a MEK-mediated disorder or disease, or a MEK-mediated dermal disorder or disease, where the subject is in need thereof.

In some embodiments, the compounds described herein are used for treatment of a MEK-inhibitor responsive disorder or disease, a MEK-inhibitor responsive dermal disorder or disease, a MEK-mediated disorder or disease, or a MEK-mediated dermal disorder or disease, where the subject is in need thereof.

Assay Methods

Compounds can be assayed for efficacy in treating a MEK-inhibitor responsive disorder or disease, a MEK-inhibitor responsive dermal disorder or disease, a MEK-mediated disorder or disease, or a MEK-mediated dermal disorder or disease where the subject is in need thereof according to any assay known to those of skill in the art. Exemplary assay methods are provided elsewhere herein.

VII. Combination Therapies

In some embodiments, the compounds and compositions provided herein are useful in methods of treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof, that comprise further administration of a second agent effective for the treatment of dermal disorders or diseases. The second agent can be any agent known to those of skill in the art to be effective for the treatment of dermal disorders or diseases, including those currently approved by the United States Food and Drug Administration, or other similar body of a country foreign to the United States.

In some embodiments, a compound provided herein is administered in combination with one second agent. In further embodiments, a compound provided herein is administered in combination with two second agents. In still further embodiments, a compound provided herein is administered in combination with two or more second agents.

In some embodiments, the methods encompass the step of administering to the subject in need thereof an amount of a compound effective for the treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof in combination with a second agent effective for the treatment or prevention of a MEK-inhibitor responsive disorder or disease, a MEK-inhibitor responsive dermal disorder or disease, a MEK-mediated disorder or disease, or a MEK-mediated dermal disorder or disease where the subject is in need thereof. The compound can be any compound as described herein, and the second agent can be any second agent described in the art or herein. In some embodiments, the compound is in the form of a pharmaceutical composition or dosage form, as described elsewhere herein.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of a MEK-inhibitor responsive disorder or disease, a MEK-inhibitor responsive dermal disorder or disease, a MEK-mediated disorder or disease, or a MEK-mediated dermal disorder or disease where the subject is in need thereof. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the MEK-inhibitor responsive disorder or disease, the MEK-inhibitor responsive dermal disorder or disease, the MEK-mediated disorder or disease, or the MEK-mediated dermal disorder or disease or a disorder to be alleviated. It is to be further understood that for any particular subject, specific dosage regimens and schedules should be adjusted over time according to the individual need and the professional judgment of the person administering or supervising the administration of the compositions.

In some embodiments, dosages of the second agents to be used in a combination therapy are provided herein. In some embodiments, dosages lower than those which have been or are currently being used to treat a MEK-inhibitor responsive disorder or disease, a MEK-inhibitor responsive dermal disorder or disease, a MEK-mediated disorder or disease, or a MEK-mediated dermal disorder or disease are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics 9$^{th}$ Ed, Mc-Graw-Hill, New York; Physician's Desk Reference (PDR) 57$^{th}$ Ed., 2003, Medical Economics Co., Inc., Montvale, NJ; which are incorporated herein by reference in their entirety.

The disclosure provides combination treatments by administration of a soft MEK inhibitor described herein with one or more additional agent(s). In some embodiments, the one or more additional agent(s) is selected from:

agents that treat acne (e.g., Accutane, Azelaic acid, Benzoil Peroxide, Salicylic acid);

analgesics (e.g., Acetaminophen, Capsaicin), e.g., a Cox2 Inhibitor, e.g. Celecoxib);

anesthetics (e.g., Benzocaine, Benzocaine/Menthol, Dibucaine, Diperodon, Lidocaine, Lidocaine/Prilocaine, Pramoxine);

anti-infectives (e.g., Crotamiton);

anti-pruritus (e.g., Ammonium lactate, Benzocaine, an ascomycin macrolactam, e.g., Pimecrolimus);

anti-prurittus/5HT3 receptor antagonists (e.g., Ondansetron);

antibiotics (e.g., clindamycin, doxycycline, erythromycin, tetracycline);

anticholinergic antiemetics (e.g., diphenhydramine);

antifibrotics (e.g., Collagenase, Pirfenidone);

antihistamines (e.g., Triprolidine (Actifed®), Fexofenadine (Allergra®, Allegra® D-12, Allegra®-24), Astepro/Astelin Nasal Spray (Azalastine) (Dymista®), Hydroxyzine hydrochloride (Atarax®), Diphenhydramine Hydrochloride (Benadryl®), Brompheniramine (Dimetapp® Cold and Allergy Elixir), Zyrtec® (Cetirizine), Chlor-Trimeton® (Chlorpheniramine), Descoratadine (Clarinex®, Clarinex® D-12, and Clarinex® D-24), Loratadine (Claritin®, Claritin® D-12, Claritin® D-24, and Alavert®), Dimenhydrinate (Dramamine®), Diphenhydramine (Benadryl® Allergy, Nytol®, Sominex®), Doxylamine (Vicks® NyQuil®, Alka-Seltzer® Plus Night-Time Cold Medicine), Cyproheptadine (Periactin®), Promethazine (Phenergan®), Acrivastine (Semprex®, Semprex®-D), Clemastine (Tavist®), doxylamine (Unisom®), Levocetirizine (Xyzal®);

mast cell stabalizers (e.g. Beta2-adrenergic agonists, Cromoglicic acid, cromolyn sodium, Gastrocrom®, Ketotifen, Methylxanthines, Omalizumab, Pemirolast, Quercetin, Ketotifen (Zaditen®));

anti-inflammatory agents (e.g., NSAID (e.g. Aspirin, Choline and magnesium salicylates, Diclofenac potassium (Cataflam®), Diclofenac sodium (Voltaren®, Voltaren® XR), Diclofenac sodium with misoprostol (Arthrotec®), Diflunisal (Dolobid®), Etodolac (Lodine®, Lodine® XL), Fenoprofen calcium (Nalfon®), Flurbiprofen (Ansaid®), Ibuprofen (Advil®, Motrin®, Motrin® IB, Nuprin®), Indomethacin (Indocin®, Indocin® SR), Ketoprofen (Actron®, Orudis®, Orudis® KT, Oruvail®), Magnesium salicylate (Arthritab, Bayer® Select, Doan's Pills, Magan, Mobidin, Mobogesic) Meclofenamate sodium (Meclomen®), Mefenamic acid (Ponstel®), Meloxicam (Mobic®), Nabumetone (Relafen®), Naproxen (Naprosyn®, Naprelan®), Naproxen sodium (Aleve®, Anaprox®), Oxaprozin (Daypro®), Piroxicam (Feldene®), Rofecoxib (Vioxx®), Salsalate (Amigesic, Anaflex 750, Disalcid, Marthritic, Mono-Gesic, Salflex, Salsitab), Sodium salicylate, Sulindac (Clinoril®), Tolmetin sodium (Tolectin®), Valdecoxib (Bextra®));

Receptor Tyrosine Kinase Inhibitor (e.g. Sunitinib);

Alkylating Agents (e.g., Dacarbazine, Carboplatin);

CDK 4/6 Inhibitors (e.g., LEE011);

PKC Inhibitors (e.g., AEB071);

MAPK inhibitors (e.g., RAS Inhibitors/Farnesyltransferase inhibitor (e.g. Tipifarnib), Raf Kinase Inhibitor (e.g. Sorafenib (BAY 43-9006, Nexavar), Vemurafenib, Dabrafenib, LGX818, TAK-632, MLN2480, PLX-4720), ERK Inhibitors (e.g., SCH772984, VTX11e);

PI3K Inhibitor (e.g., LY294002);

AKT Inhibitor (e.g., MK 2206);

PI3K/AKT Inhibitor (e.g. buparlisib, Cixutumumab);

mTOR Inhibitors (e.g. Topical Rapamycin, RAD001 (Everolimus/Rapamycin), Temsirolimus, Sirolimus);

Tyrosine Kinase Inhibitors (e.g. Imatinib (Gleevec®), Cabozantinib (inhibitor of tyrosine kinases c-Met and VEGFR2), Nilotinib (Tasigna®);

VEGF Inhibitor (e.g. Ranibizumab (Lucentis®), Cediranib);

Immune Response Modifier (e.g. Topical Imiquimod, Interferon, PEG Interferon);

Calcium Channel Blocker (e.g. Avocil (Mederma)/15% Verapamil, vitamin D separately, Doxycyline Injections);

Statin (e.g. Lovastatin, Methotrexate, Vinblastine, Pregabalin, Temozolomide, PLX3397);

HDAC Inhibitor (e.g. AR-42);

HSP-90 Inhibitors (e.g. Ganetespib);

retinoids (e.g. adapalene, Isotretinoin, tazarotene, tretinoin);

steroids (e.g. Alclometasone, Amcinonide, Betamethasone, Betamethasone dipropionate, Betamethasone dipropionate, augmented, Budesonide, Clobetasol propionate, Cortisone, Desonide, Dexamethasone, Diflorasone diacetate, Fluocinolone acetonide, Fluocinonide, Flurandrenolide, Fluticasone propionate, Halobetasol propionate, Halocinonide, Hydrocortisone, Hydrocortisone butyrate, Hydrocortisone valerate, Methylprednisolone, Mometasone, Mometasone furoate, Prednicarbate, Prednisolone, Prednisone, Triamcinolone, Triamcinolone acetonide);

topical calcineurin inhibitors (e.g., pimecrolimus (Elidel® Cream 1%, Novartis, tacrolimus (Protopic® Ointment, Astellas)); and Non-pharmaceutical Interventions (e.g. photodynamic Therapy (Levulan Kerastick Topical+light), Electrodesication (ED), YAG Laser).

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In some embodiments, two or more therapies are administered within the same patient visit. In some embodiments, the compound provided herein and the second agent are administered concurrently.

In some embodiments, the compound provided herein and the second agent are administered at about 2 to 4 days apart, at about 4 to 6 days apart, at about 1 week part, at about 1 to 2 weeks apart, or more than 2 weeks apart.

In some embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In some embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In some embodiments, a compound provided herein and a second agent are administered to a patient, in some embodiments, a mammal, such as a human, in a sequence and within a time interval such that the compound provided herein can act together with the other agent to provide an increased benefit than if they were administered otherwise.

In some embodiments, the second active agent can be administered at the same time or sequentially in any order at different points in time; however, if not administered at the same time, they should be administered sufficiently close in time so as to provide the desired therapeutic or prophylactic effect. In some embodiments, the compound provided herein and the second active agent exert their effect at times which overlap. Each second active agent can be administered separately, in any appropriate form and by any suitable route. In some embodiments, the compound provided herein is administered before, concurrently or after administration of the second active agent.

In some embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In some embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In some embodiments, courses of treatment are administered concurrently to a patient, i.e., individual doses of the second agent are administered separately yet within a time interval such that the compound provided herein can work together with the second active agent. In some embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In some embodiments, the compound provided herein is administered concurrently with one or more second agents in the same pharmaceutical composition. In some embodiments, a compound provided herein is administered concurrently with one or more second agents in separate pharmaceutical compositions. In some embodiments, a compound provided herein is administered prior to or subsequent to administration of a second agent. Also contemplated are administration of a compound provided herein and a second agent by the same or different routes of administration, e.g., oral and parenteral. In some embodiments, when the compound provided herein is administered concurrently with a second agent that potentially produces adverse side effects including, but not limited to, toxicity, the second active agent can advantageously be administered at a dose that falls below the threshold that the adverse side effect is elicited.

VIII. Examples

General Synthetic Methods

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art. As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMSO (dimethylsulfoxide); DMSO-d$_6$ (deuterated dimethylsulfoxide); EtOAc (ethyl acetate); MeOH (methanol); Tces (2,2,2-trichloroethoxysulfonyl); —Si(tert-Bu)(Ph)$_2$ and —Si$^t$BuPh$_2$ (tert-butyl-diphenylsilyl); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Compounds of formula (Ia) can be prepared according to Scheme 1, as shown in FIG. 1, in which subscript n is 0; $R^1$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl)amino-$C_1$-$C_6$ alkyl, heterocycloalkyl, heterocycloalkyl-$C_1$-$C_6$ alkyl, $R^5$—C(O)—$C_1$-$C_6$ alkyl, or —OH, wherein each of the $C_3$-$C_8$ cycloalkyl and heterocycloalkyl groups is unsubstituted or substituted with one to six $R^6$; $R^2$, $R^{2a}$, $R^{3a}$, $R^{3b}$, $R^5$, and $R^6$ are as defined in any aspect, embodiment, or claim as described herein. In some embodiments, $R^{3a}$ and $R^{3b}$ are each hydrogen.

Starting from commercially-available or routinely-accessible pyridines of formula (101), and commercially-available methyl chloroformate, compounds of formula (102) can be prepared by methods apparent to those of skill in the art. A compound of formula (102) is then reacted with a compound of formula (103) in the presence of Cs$_2$CO$_3$ and a catalyst, for example PdXPhos G2, wherein the compound of formul (103) is prepared from pinacolborane and ethyl vinyl ether. Cyclization of the compound of formula (104) under an acidic conditions provides the intermediate of formula (105). Various commercially-available or routinely-accessible amines or protected amines of RiNH$_2$ can react with the intermediate of formula (105) to provide compounds of formula (106). Compounds of formula (Ia) can be prepaed by a coupling reaction of the compounds of formula (106) with commercially-available or routinely-accessible anilines by methods apparent to those of skill in the art, followed by optional deprotection. In some embodiments of compounds of formula (Ia) wherein $R^1$ is HOC(O)—$C_1$-$C_6$ alkyl, after further activation of the —C(O)OH group by methods known in the art, these compounds are converted to compounds of formula (Ia), in which $R^1$ is $R^5C(O)$—$C_1$-$C_6$ alkyl.

Compounds of formula (Ia) can be prepared according to Scheme 2, as shown in FIG. 2, in which subscript n is 0; $R^1$ is —OR$^4$; and $R^2$, $R^{2a}$, $R^{3a}$, $R^{3b}$, and $R^4$ are as defined in any aspect, embodiment, or claim as described herein. In some embodiments, $R^{3a}$ and $R^{3b}$ are each hydrogen.

Starting from the common intermediate of formula (104) as shown in Scheme 1, various commercially-available or routinely-accessible hydroxyamines or pretected hydroxyamines of R$^4$ONH$_2$ can react with the compound of formula (104) to provide compounds of formula (107). Cyclization of the compound of formula (107) under a base provides a compound of formula (108) (note any ester group in $R^1$ is also hydrolyzed to a corresponding acid). Compounds of formula (Ia) can be prepared by a coupling reaction of the compounds of formula (108) with commercially-available or routinely-accessible anilines by methods apparent to those of skill in the art, followed by optional deprotection. In some embodiments of compounds of formula (Ia) wherein $R^1$ is —OR$^4$ and $R^4$ is HOC(O)—$C_1$-$C_6$ alkyl, after further activation of the C(O)OH group by methods known in the art, these compounds are converted to compounds of formula (Ia), in which $R^1$ is —OR$^4$ and $R^4$ is $R^5C(O)$—$C_1$-$C_6$ alkyl. In some embodiments, when $R^1$ is —OH, the corresponding compound of formula (Ia) is prepared according to Scheme 1.

Compounds of formula (Ib) can be prepared according to Scheme 3 as shown in FIG. 3, in which subscript n is 0 and $R^1$, $R^2$, $R^{2a}$, $R^{3a}$, and $R^{3b}$ are as defined in any aspect, embodiment, or claim as described herein. In some embodiments, $R^{3a}$ and $R^{3b}$ are each hydrogen.

Starting from the common intermediate of formula (104) as shown in Scheme 1, various commercially-available or routinely-accessible amines, hydroxyamines, pretected amines, or protected hydroxyamines of R$^1$NH$_2$ can react with the compound of formula (104) to provide compounds of formula (109). Reductive cyclization of the compound of formula (109) under a reducing agent (e.g., NaCNBH$_3$) provides a compound of formula (110) (note that an ester group in $R^1$ is also hydrolyzed to a corresponding acid). Compounds of formula (Ia) can be prepared by a coupling reaction of the compounds of formula (110) with commercially-available or routinely-accessible anilines by methods apparent to those of skill in the art, followed by optional deprotection. In some embodiments of compounds of formula (Ia) wherein $R^1$ is HOC(O)—$C_1$-$C_6$ alkyl or —OR$^4$ and $R^4$ is HOC(O)—$C_1$-$C_6$ alkyl, after further activation of the C(O)OH group by methods known in the art, these compounds are converted to compounds of formula (Ia), in which $R^1$ is $R^5C(O)$—$C_1$-$C_6$ alkyl or —OR$^4$ and $R^4$ is $R^5C(O)$—$C_1$-$C_6$ alkyl.

Utilizing the Exemplary Preparation Schemes provided herein and procedures known to one of ordinary skill in the art, the compounds in Tables 1 and 2 can be prepared.

General Methods

NMR Spectroscopy $^1$H NMR spectra were recorded at 400 MHz on a Bruker Avance III NMR spectrometer. Samples were prepared in deuterated chloroform (CDCl$_3$) or dimethylsulphoxide (DMSO-d$_6$) and the raw data were processed using the ACD NMR software.

UPLC-MS Analysis

LCMS analysis was conducted on a Waters Acquity UPLC system consist of an Acquity i-Class Sample Manager-FL, Acquity i-Class Binary Solvent Manager and Acquity i-Class UPLC Column Manager. UV detection was achieved using an Acquity i-Class UPLC PDA detector (scanning from 210-400 nm), whereas mass detection was achieved using an Acquity QDa detector (mass scanning from 100-1250 Da; positive and negative modes simultaneously). A Waters Acquity UPLC BEH C18 column (2.1×50 mm, 1.7 μm) was used to achieve the separation of the analytes.

Samples were prepared by dissolving (with or without sonication) into 1 mL of a 1:1 (v/v) mixture of MeCN in $H_2O$. The resulting solutions were filtered through a 0.2 m syringe filter before being submitted for analysis. All of the solvents (including formic acid and 36% ammonia solution) used were used as the HPLC grade.

Four different analytical methods were used for analyzing compounds as described herein. Each of four analytical methods is detailed as follows:

Acidic run (2 min): 0.100 v/v Formic acid in water [Eluent A]; 0.10% v/v Formic acid in MeCN [Eluent B]; Flow rate 0.8 mL/min; injection volume 2 μL and 1.5 min equilibration time between samples.

| Time (min) | Eluent A (%) | Eluent B (%) |
| --- | --- | --- |
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Acidic run (4 min): 0.10% v/v formic acid in water [Eluent A]; 0.10% v/v formic acid in MeCN [Eluent B]; Flow rate 0.8 mL/min; injection volume 2 μL and 1.5 min equilibration time between samples.

| Time (min) | Eluent A (%) | Eluent B (%) |
| --- | --- | --- |
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Basic run (2 min): 0.10% ammonia in water [Eluent A]; 0.1% ammonia in MeCN [Eluent B]; Flow rate 0.8 mL/min; injection volume 2 μL and 1.5 min equilibration time between samples.

| Time (min) | Eluent A (%) | Eluent B (%) |
| --- | --- | --- |
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic run (4 min): 0.1% ammonia in water [Eluent A]; 0.1% ammonia in MeCN [Eluent B]; Flow rate 0.8 mL/min; injection volume 2 μL and 1.5 min equilibration time between samples.

| Time (min) | Eluent A (%) | Eluent B (%) |
| --- | --- | --- |
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Example 1: (R)-2-(2,3-Dihydroxypropyl)-8-(2-fluoro-4-iodophenylamino)-2,6-naphthyridin-1(2H)-one Step 1: Methyl 3-bromo-5-fluoroisonicotinate To a solution of dry diisopropylamine (8.8 mL, 62.5 mmol) in dry THE (300 mL) stirred at 0° C. n-BuLi (2.5M in hexanes, 25 mL, 62.5 mmol) was added. The reaction mixture was stirred for 30 min at room temperature, then cooled down to −78° C. and a solution of 3-bromo-5-fluoropyridine (10 g, 56.8 mmol) in dry THF (300 mL) was added. The reaction mixture was stirred for 1 h and treated with methyl chloroformate (5.3 mmol, 68.2 mmol). The reaction mixture was stirred for 1.5 h and then was quenched with a saturated $NH_4Cl$ aqueous solution at 0° C., extracted with EtOAc (3×100 mL), washed with $H_2O$ (100 mL) and brine (100 mL), dried over $Na_2SO_4$ and concentrated in vacuo. The crude material was purified by flash column chromatography (Silica, 0-7% EtOAc in hexanes) to give the product (10.43 g, 78%) as a yellowish liquid. UPLC-MS (Acidic Method, 2 min): rt 0.86 min, m/z 234.0/236.0 $[M+H]^+$.

$^1$H NMR (400 MHz, $CDCl_3$): δ ppm 8.69 (t, J=0.5 Hz, 1H), 8.57 (d, J=8.4 Hz, 1H), 4.08 (s, 3H).

Step 2: 2-(2-Ethoxyvinyl)-4,4,5,5-tetramethyl-1,3,2-dioxaborolane (the Compound of Formula (103))

To a mixture of pinacolborane (20 g, 156 mmol) and ethyl vinyl ether (61.4 mL, 640 mmol) was added palladium(II) acetate (0.176 g, 0.781 mmol) carefully due to an exothermic process. The reaction mixture was stirred at room temperature for 18 h. Then the reaction mixture was concentrated in vacuo and the residue was passed through a silica plug (0-10% EtOAc in hexanes) to give the product (24.6 g, 85%) as a yellow liquid. UPLC-MS (Acidic Method, 2 min): rt 0.92 and 1.03 min, m/z 199.2 [M+H]+. $^1$H NMR (400 MHz, CDCl$_3$): δ ppm (Note: a mixture of E:Z isomers 1.25:1) 7.03 (d, J=14.4 Hz, 1.25H), 6.64 (d, J=0.4 Hz, 1H), 4.43 (d, J=14.4 Hz, 1.25H), 4.11 (dd, J=7.8, 4.4 Hz, 1H), 3.94 (q, J=7.1 Hz, 2H), 3.84 (q, J=7.1 Hz, 2.5H), 1.28-1.24 (m, 31H), 0.95-0.84 (m, 3H).

Step 3: Methyl 3-(2-ethoxyvinyl)-5-fluoroisonicotinate (a Compound of Formula (104))

A degassed solution of methyl 3-bromo-5-fluoroisonicotinate (10 g, 42.70 mmol), 2-(2-ethoxyvinyl)-4,4,5,5-tetramethyl-1,3,2-dioxaborolane (12.7 g, 64.05 mmol), Cs$_2$CO$_3$ (48.7 g, 49.45 mmol) and PdXPhos G2 catalyst (3.4 g, 4.27 mmol) in THF/H$_2$O (9:1 v/v, 90:10 mL) was stirred at 85° C. for 18 h. The reaction mixture was diluted with EtOAc (100 mL) and filtered through a Celite pad. The organic filtrate was washed with H$_2$O (100 mL), brine (100 mL), dried over Na$_2$SO$_4$, and concentrated in vacuo. The crude material was purified by flash column chromatography (Silica, 0-25% EtOAc in hexanes) to give the product (7.07 g, 74%) as a brown oil. UPLC-MS (Acidic Method, 2 min): rt 1.01 and 1.10 min, m/z 226.1 [M+H]+. $^1$H NMR (400 MHz, CDCl$_3$): δ ppm (Note: a mixture of E:Z isomers 1.15:1) 9.18-9.13 (m, 1H), 8.48 (s, 1.15H), 8.30 (dd, J=5.2, 0.8 Hz, 2.15H), 7.03 (d, J=12.9 Hz, 1.15H), 6.41 (dd, J=7.1, 0.7 Hz, 1H), 5.91 (d, J=12.9 Hz, 1.15H), 5.27 (d, J=7.1 Hz, 1H), 4.05 (q, J=7.1 Hz, 2H), 4.01-3.90 (m, 8.75H), 1.37 (td, J=7.1, 2.8 Hz, 6.5H).

Step 4: 8-Fluoro-1H-pyrano[4,3-c]pyridin-1-one hydrochloride (a Compound of Formula (105))

To methyl 3-(2-ethoxyvinyl)-5-fluoroisonicotinate (2.07 g, 9.2 mmol) was added 4M HCl (26 mL, 104 mmol) and the reaction mixture was stirred at 100° C. for 18 h. The reaction mixture was cooled down and the formed precipitate was isolated by filtration, washed with dioxane (3×5 mL) and dried in vacuo to give the product (0.93 g, 50%) as a pale-brown solid. UPLC-MS (Acidic Method, 2 min): rt 0.60, m/z 166.0 [M+H]+. $^1$H NMR (400 MHz, CDCl$_3$): δ ppm 8.69 (s, 1H), 8.63 (d, J=2.2 Hz, 1H), 7.41 (d, J=5.6 Hz, 1H), 6.60 (dd, J=5.6, 2.5 Hz, 1H).

Step 5: (R)-2-((2,2-Dimethyl-1,3-dioxolan-4-yl)methyl)-8-fluoro-2,6-naphthyridin-1(2H)-one To a solution of 8-fluoro-1H-pyrano[4,3-c]pyridin-1-one hydrochloride (300 mg, 1.82 mmol) in MeOH (13 mL) was added (R)-(2,2-dimethyl-1,3-dioxolan-4-yl)methanamine (334 mg, 2.55 mmol) and the reaction mixture was heated at 80° C. for 72 h. The reaction mixture was concentrated in vacuo and the residue was dissolved in EtOAc, washed with H$_2$O (30 mL), brine (30 mL), dried over Na$_2$SO$_4$, and concentrated in vacuo. The crude material was purified by flash column chromatography (Silica, 0-80% EtOAc in hexanes) to give the product (94 mg, 19%) as an off-white solid. UPLC-MS (Acidic Method, 2 min): rt 0.84 min, m/z 279.2 [M+H]+. $^1$H NMR (400 MHz, CDCl$_3$): δ 8.74 (s, 1H), 8.46 (d, J=3.1 Hz, 1H), 7.37 (d, J=7.4 Hz, 1H), 6.55 (dd, J=7.4, 2.3 Hz, 1H), 4.52 (qd, J=6.6, 3.0 Hz, 1H), 4.39 (dd, J=13.8, 3.0 Hz, 1H), 4.16 (dd, J=8.8, 6.5 Hz, 1H), 3.91 (dd, J=13.8, 7.0 Hz, 1H), 3.74 (dd, J=8.8, 6.3 Hz, 1H), 1.43 (s, 3H), 1.34 (s, 3H).

Step 6: (R)-2-((2,2-Dimethyl-1,3-dioxolan-4-yl)methyl)-8-(2-fluoro-4-iodophenylamino)-2,6-naphthyridin-1(2H1)-one A solution of 2-fluoro-4-iodoaniline (49 mg, 0.21 mmol) in dry THF (1 mL) stirred at −78° C. was treated with LiHMDS (1M in THF, 0.3 mL, 0.3 mmol) and the reaction mixture was stirred for 10 min. Then a solution of (R)-2-((2,2-dimethyl-1,3-dioxolan-4-yl)methyl)-8-fluoro-2,6-naphthyridin-1(2H)-one (60 mg, 0.216 mmol) in dry THF (1 mL) was added and the reaction mixture was stirred at −78° C. for 15 min, and then let to warm up to room temperature. The reaction mixture was quenched with a saturated NH$_4$Cl aqueous solution (1 mL) at 0° C. and extracted with EtOAc (3×7 mL). The combined organic phase was washed with H$_2$O (7 mL), brine (7 mL), dried over Na$_2$SO$_4$, and concentrated in vacuo. The crude material was purified by flash column chromatography (Silica, 0-50% EtOAc in hexanes) to give the product (68 mg, 64%) as a yellow solid. UPLC-MS (Acidic Method, 2 min): rt 1.17 min, m/z 496.1 [M+H]$^+$.
$^1$H NMR (400 MHz, CDCl$_3$): δ 10.56 (s, 1H), 8.41 (s, 1H), 8.28 (s, 1H), 7.56-7.43 (m, 2H), 7.33 (t, J=8.4 Hz, 1H), 7.25 (d, 1H), 6.50 (d, J=7.4 Hz, 1H), 4.51 (qd, J=6.5, 3.1 Hz, 1H), 4.36 (dd, J=13.8, 3.1 Hz, 1H), 4.16 (dd, J=8.7, 6.5 Hz, 1H), 3.88 (dd, J=13.8, 7.0 Hz, 1H), 3.75 (dd, J=8.7, 6.2 Hz, 1H), 1.44 (s, 3H), 1.35 (s, 3H).

Step 7: (R)-2-(2,3-Dihydroxypropyl)-8-(2-fluoro-4-iodophenylamino)-2,6-naphthyridin-1(2H)-one A solution of (R)-2-((2,2-dimethyl-1,3-dioxolan-4-yl)methyl)-8-(2-fluoro-4-iodophenylamino)-2,6-naphthyridin-1(2H)-one (68 mg, 0.137 mmol) in dioxane (3.5 mL) was treated with 4M HCl in dioxane (0.086 mL) and the reaction mixture was stirred at room temperature for 18 h. The reaction mixture was concentrated in vacuo to give the product (62 mg, 100%) as an orange solid. UPLC-MS (Acidic Method, 2 min): rt 0.87 min, m/z 456.0 [M+H]$^+$. $^1$H NMR (400 MHz, CD$_3$CN): δ 11.13 (s, 1H), 8.30 (s, 1H), 7.94 (s, 1H), 7.69 (dd, J=10.1, 1.9 Hz, 1H), 7.61 (dd, J=16.5, 7.9 Hz, 2H), 7.36 (t, J=8.4 Hz, 1H), 6.75 (d, J=7.3 Hz, 1H), 4.31 (dd, J=13.5, 3.2 Hz, 1H), 4.03-3.91 (m, 1H), 3.87 (dd, J=13.4, 8.2 Hz, 1H), 3.58-3.44 (m, 2H).

Example 2: (S)-2-(2,3-Dihydroxypropyl)-8-(2-fluoro-4-iodophenylamino)-2,6-naphthyridin-1(2H)-one Step 1: (S)-2-((2,2-Dimethyl-1,3-dioxolan-4-yl)methyl)-8-fluoro-2,6-naphthyridin-1(2H)-one To a solution of 8-fluoro-1H-pyrano[4,3-c]pyridin-1-one hydrochloride (500 mg, 3.03 mmol) in MeOH (22 mL) was added (S)-(2,2-dimethyl-1,3-dioxolan-4-yl)methanamine (556 mg, 4.24 mmol) and the reaction mixture was stirred at 80° C. for 72 h. The reaction mixture was concentrated in vacuo and the residue was dissolved in EtOAc, washed with H$_2$O (50 mL), brine (50 mL), dried over Na$_2$SO$_4$, and concentrated in vacuo. The crude material was purified by flash column chromatography (Silica, 0-100% EtOAc in hexanes) to give the product (165 mg, 20%) as a yellow solid. UPLC-MS (Acidic Method, 2 min): rt 0.76 min, m/z 279.1 [M+H]$^+$.

$^1$H NMR (400 MHz, CDCl$_3$): δ 8.74 (s, 1H), 8.46 (d, J=3.1 Hz, 1H), 7.37 (d, J=7.4 Hz, 1H), 6.55 (dd, J=7.4, 2.3 Hz, 1H), 4.52 (qd, J=6.5, 3.0 Hz, 1H), 4.39 (dd, J=13.8, 3.0 Hz, 1H), 4.16 (dd, J=8.8, 6.5 Hz, 1H), 3.90 (dd, J=13.8, 7.0 Hz, 1H), 3.74 (dd, J=8.8, 6.3 Hz, 1H), 1.43 (s, 3H), 1.34 (s, 3H).

Step-2: (S)-2-((2,2-Dimethyl-1,3-dioxolan-4-yl)methyl)-8-(2-fluoro-4-iodophenylamino)-2,6-naphthyridin-1(2H)-one A solution of 2-fluoro-4-iodoaniline (53 mg, 0.222 mmol) in dry THF (1 mL) stirred at −78° C. was treated with LiHMDS (1M in THF, 0.33 mL, 0.33 mmol) and the reaction mixture was stirred for 10 minutes. Then, a solution of (S)-2-((2,2-dimethyl-1,3-dioxolan-4-yl)methyl)-8-fluoro-2,6-naphthyridin-1(2H)-one (65 mg, 0.234 mmol) in dry THF (1 mL) was added and the reaction mixture was stirred at −78° C. for 15 minutes, then let to warm up to room temperature. The reaction mixture was quenched with a saturated NH$_4$Cl aqueous solution (1 mL) at 0° C. and extracted with EtOAc (3×7 mL). The combined organic phase was washed with H$_2$O (7 mL), brine (7 mL), dried over Na$_2$SO$_4$, and concentrated in vacuo. The crude material was purified by flash column chromatography (Silica, 0-50% EtOAc in hexanes) to give the product (77 mg, 66%) as a yellow solid. UPLC-MS (Acidic Method, 2 min): rt 1.14 min, m/z 496.0 [M+H]$^+$.

$^1$H NMR (400 MHz, CDCl$_3$): δ 10.55 (s, 1H), 8.40 (s, 1H), 8.27 (s, 1H), 7.55-7.42 (m, 2H), 7.32 (t, J=8.4 Hz, 1H), 7.24 (d, 1H), 6.49 (d, J=7.3 Hz, 1H), 4.50 (qd, J=6.6, 3.2 Hz, 1H), 4.35 (dd, J=13.8, 3.1 Hz, 1H), 4.15 (dd, J=8.8, 6.5 Hz, 1H), 3.87 (dd, J=13.8, 7.0 Hz, 1H), 3.74 (dd, J=8.7, 6.2 Hz, 1H), 1.43 (s, 3H), 1.34 (s, 3H).

Step 3: (S)-2-(2,3-Dihydroxypropyl)-8-(2-fluoro-4-iodophenylamino)-2,6-naphthyridin-1(2H)-one A solution of (S)-2-((2,2-dimethyl-1,3-dioxolan-4-yl)methyl)-8-(2-fluoro-4-(trimethylsilyl)phenyl-amino)-2,6-naphthyridin-1(2H)-one (67 mg, 0.136 mmol) in dioxane (3.5 mL) was treated with 4M HCl in 1,4-dioxane (85 μL) and the reaction mixture was stirred at ambient temperature for 18 h. The reaction mixture was concentrated in vacuo and the crude material was purified by preparatory HPLC to give the product (16 mg, 26%) as a yellow solid. UPLC-MS (Acidic Method, 2 min): rt 1.02 min, m/z 456.1 [M+H]$^+$. $^1$H NMR (400 MHz, CD$_3$CN): δ 10.73 (s, 1H), 8.35 (d, J=1.3 Hz, 1H), 8.32 (s, 1H), 7.62 (dd, J=10.4, 2.0 Hz, 1H), 7.55 (ddd, J=8.5, 2.1, 1.0 Hz, 1H), 7.44 (t, J=8.5 Hz, 1H), 7.37 (d, J=7.4 Hz, 1H), 6.60 (d, J=7.4 Hz, 1H), 4.23 (dd, J=13.4, 3.6 Hz, 1H), 3.95 (m, 1H), 3.85 (dd, J=13.4, 7.8 Hz, 1H), 3.54-3.46 (m, 2H).

Example 3: 2-(3-Aminopropyl)-8-(2-fluoro-4-iodophenylamino)-2,6-naphthyridin-1(2H)-one hydrochloride Step 1: tert-Butyl 3-(8-fluoro-1-oxo-2,6-naphthyridin-2(1H)-yl)propylcarbamate A solution of 8-fluoro-1H-pyrano[4,3-c]pyridin-1-one hydrochloride (0.50 g, 2.48 mmol) and tert-butyl 3-aminopropylcarbamate (0.74 g, 4.24 mmol) in MeOH (22 mL) was heated at 80° C. for 18 h and then concentrated in vacuo. The crude residue was treated with EtOAc and the collected organic phases were washed with brine, dried over Na$_2$SO$_4$, filtered and concentrated in vacuo to give the crude product (1.02 g, 35% pure) that was taken to the next step without further purification. UPLC-MS (Acidic Method, 2 min): rt 0.97 min, m/z 322.1 [M+H]$^+$.

Step 2: tert-Butyl 3-(8-(2-fluoro-4-iodophenylamino)-1-oxo-2,6-naphthyridin-2(1H)-yl)propylcarbamate A solution of 2-fluoro-4-iodoaniline (680 mg, 2.87 mmol) in dry THF (15 mL) stirred at −78° C. under $N_2$ was treated with LiHMDS (1M in THF, 4.23 mL, 4.23 mmol) added dropwise. The reaction mixture was stirred for 15 min at −78° C. and then a suspension of tert-butyl 3-(8-fluoro-1-oxo-2,6-naphthyridin-2(1H)-yl)propylcarbamate (970 mg, 35% pure, 1.06 mmol) in dry THF (15 mL) was added. The reaction mixture was further stirred at −7° C. and then let to warm up to room temperature. After 1 h the reaction mixture was re-cooled down to −78° C. and treated with additional portions of LiHMDS (1M in THF, 4.23 mL, 4.23 mmol) added dropwise; this addition was repeated once more. The reaction mixture was further stirred for 1 h and let to warm up to room temperature. Then the reaction mixture was quenched with a saturated $NH_4Cl$ aqueous solution at 0° C. and extracted with EtOAc. The combined organic phase was washed with brine, dried over $Na_2SO_4$, filtered and concentrated in vacuo to give the crude material which was purified by flash column chromatography (Silica, 0-90% EtOAc in hexane) to give the product (73 mg, 13%). UPLC-MS (Acidic Method, 2 min): rt 1.28 min, m/z 539.0 [M+H]$^+$. $^1$H NMR (400 MHz, CDCl$_3$): δ ppm 10.57 (s, 1H), 8.38 (d, J=1.3 Hz, 1H), 8.26 (s, 1H), 7.52 (dd, J=9.8, 2.0 Hz, 1H), 7.46 (dt, J=8.5, 1.5 Hz, 1H), 7.31 (t, J=8.3 Hz, 1H), 7.16 (d, J=7.3 Hz, 1H), 6.52 (d, J=7.3 Hz, 1H), 5.01 (br s, 1H), 4.03 (t, J=6.7 Hz, 2H), 3.18 (q, J=6.3 Hz, 2H), 1.96 (p, J=6.6 Hz, 2H), 1.44 (s, 9H).

Step 3: 2-(3-Aminopropyl)-8-(2-fluoro-4-iodophenylamino)-2,6-naphthyridin-1(2H)-one hydrochloride A solution of tert-butyl 3-(8-(2-fluoro-4-iodophenylamino)-1-oxo-2,6-naphthyridin-2(1H)-yl)propylcarbamate (73 mg, 0.136 mmol) in dry dioxane (1 mL) stirred at room temperature was treated with HCl solution (4 N in dioxane, 50 µl, 0.195 mmol). After 1.5 h an additional portion of HCl solution (4 N in dioxane, 2×50 µl, 0.390 mmol) was added and the reaction mixture was further stirred for 18 h. The reaction mixture was then concentrated in vacuo to give the product (62 mg, 97%) as a yellow solid. UPLC-MS (Acidic Method, 2 min): rt 0.85 min, m/z 439.0 [M+H]$^+$. $^1$H NMR (400 MHz, DMSO-d$_6$): δ ppm 10.83 (s, 1H), 8.45 (d, J=1.6 Hz, 1H), 8.31 (s, 1H), 7.89 (br s, 3H), 7.77 (dd, J=10.4, 1.9 Hz, 1H), 7.72 (d, J=7.7 Hz, 1H), 7.58 (dd, J=8.3, 2.0 Hz, 1H), 7.50 (t, J=8.5 Hz, 1H), 6.81 (dd, J=7.2, 1.3 Hz, 1H), 4.07 (t, J=6.9 Hz, 2H), 2.84 (q, J=7.2, 6.8 Hz, 2H), 2.01 (p, J=7.0 Hz, 2H).

Example 4: 2-(8-(2-Fluoro-4-iodophenylamino)-1-oxo-2,6-naphthyridin-2(1H)-yl)acetic acid

Step 1: Methyl 2-(8-fluoro-1-oxo-2,6-naphthyridin-2(1H)-yl)acetate

A suspension of glycine methyl ester hydrochloride (0.53 g, 4.24 mmol) in MeOH (5 mL) was treated with Et$_3$N (0.59 mL, 4.24 mmol) and the resultant solution was added to a solution of 8-fluoro-1H-pyrano[4,3-c]pyridin-1-one hydrochloride (0.50 g, 2.48 mmol) in MeOH (17 mL). The reaction mixture was heated at 80° C. for 72 h and then concentrated in vacuo. The crude residue was treated with EtOAc multiple times and the collected organic phases were washed with water, brine, dried over Na$_2$SO$_4$, filtered and concentrated in vacuo to give the product (465 mg, 80%) that was taken to the next step without further purification. UPLC-MS (Acidic Method, 2 min): rt 0.71 min, m/z 237.1 [M+H]$^+$. $^1$H NMR (400 MHz, CDCl$_3$): δ ppm 8.75 (s, 1H), 8.48 (d, J=3.0 Hz, 1H), 7.16 (d, J=7.4 Hz, 1H), 6.59 (dd, J=7.3, 2.3 Hz, 1H), 4.69 (s, 2H), 3.80 (s, 3H).

Step 2: 2-(8-Fluoro-1-oxo-2,6-naphthyridin-2(1H)-yl)acetic acid

A solution of methyl 2-(8-fluoro-1-oxo-2,6-naphthyridin-2(1H)-yl)acetate (465 mg, 1.97 mmol) in MeOH (12 mL) and H₂O (12 mL) stirred at 0° C. was treated with 1M LiOH aqueous solution (3.9 mL, 3.94 mmol). The reaction mixture was stirred for 30 min and let to warm up to room temperature. Then the reaction mixture was concentrated in vacuo and the residue was extracted with EtOAc. The aqueous phase was acidified with citric acid aqueous solution (pH 2) to reach pH 3 and then was extracted with EtOAc. The combined organic phase was washed with brine, dried over Na₂SO₄, filtered and concentrated in vacuo to give the product (153 mg, 50%) as an off-white solid. UPLC-MS (Acidic Method, 2 min): rt 0.17 min, m/z 223.0 [M+H]⁺. ¹H NMR (400 MHz, DMSO-d₆): δ ppm 13.09 (s, 1H), 8.91 (s, 1H), 8.55 (d, J=3.3 Hz, 1H), 7.67 (d, J=7.3 Hz, 1H), 6.80 (dd, J=7.4, 2.4 Hz, 1H), 4.69 (s, 2H).

Step 3: 2-(8-(2-Fluoro-4-iodophenylamino)-1-oxo-2,6-naphthyridin-2(1H)-yl)acetic acid A solution of 2-fluoro-4-iodoaniline (155 mg, 0.655 mmol) in dry THF (2 mL) stirred at −78° C. under N₂ was treated with LiHMDS (1M in THF, 1.65 mL, 1.65 mmol) added dropwise. The reaction mixture was stirred for 10 min at −78° C. and then a suspension of 2-(8-fluoro-1-oxo-2,6-naphthyridin-2(1H)-yl)acetic acid (153 mg, 0.689 mmol) in dry THF (3 mL) was added. The reaction mixture was further stirred and let to warm up to room temperature. After 2.5 h the reaction mixture was re-cooled down to −78° C. and treated with additional portions of LiHMDS (1M in THF, 2×0.8 mL, 1.60 mmol) added dropwise. The reaction mixture was further stirred for 18 h and let to warm up to room temperature. Then the reaction mixture was quenched with a saturated NH₄Cl aqueous solution at 0° C. and extracted with EtOAc. The aqueous phase was acidified with citric acid aqueous solution (pH 2) to reach pH 3 and then was extracted with EtOAc. The combined organic phase was washed with brine, dried over Na₂SO₄, filtered and concentrated in vacuo to give the crude material which was purified by preparative HPLC purification to give the product (32 mg, 11%) as a yellow solid. UPLC-MS (Acidic Method, 2 min): rt 1.01 min, m/z 440.1 [M+H]⁺. ¹H NMR (400 MHz, DMSO-d₆): δ ppm 13.16 (s, 1H), 10.56 (s, 1H), 8.39 (s, 1H), 8.30 (d, J=1.2 Hz, 1H), 7.75 (dd, J=10.4, 1.9 Hz, 1H), 7.60 (d, J=7.3 Hz, 1H), 7.58-7.53 (m, 1H), 7.49 (t, J=8.5 Hz, 1H), 6.73 (d, J=7.3 Hz, 1H), 4.70 (s, 2H).

Example 5: Methyl 2-(8-(2-fluoro-4-iodophenylamino)-1-oxo-2,6-naphthyridin-2(1H)-yl)acetate A solution of 2-(8-(2-fluoro-4-iodophenylamino)-1-oxo-2,6-naphthyridin-2(1H)-yl)acetic acid (200 mg, 0.46 mmol) in MeOH (1 mL) stirred at 0° C. was treated with SOCl₂ (0.12 mL, 1.61 mmol) added dropwise. The reaction mixture was stirred for 18 h and let to warm up to room temperature. The reaction mixture was concentrated in vacuo to give the crude material which was purified by preparative HPLC purification to give the product (11 mg, 8%). UPLC-MS (Acidic Method, 2 min): rt 1.14 min, m/z 454.0 [M+H]⁺. ¹H NMR (400 MHz, DMSO-d₆): δ ppm 10.46 (s, 1H), 8.39 (s, 1H), 8.30 (d, J=1.3 Hz, 1H), 7.75 (dd, J=10.4, 1.9 Hz, 1H), 7.61 (d, J=7.3 Hz, 1H), 7.59-7.53 (m, 1H), 7.48 (t, J=8.5 Hz, 1H), 6.76 (d, J=7.3 Hz, 1H), 4.82 (s, 2H), 3.71 (s, 3H).

Example 6: 8-(2-Fluoro-4-iodophenylamino)-2-hydroxy-2,6-naphthyridin-1(2H)-one

Step 1: 8-Fluoro-2-hydroxy-2,6-naphthyridin-1(2H)-one

A suspension of hydroxyamine hydrochloride (0.29 g, 4.24 mmol) in MeOH (5 mL) was treated with Et$_3$N (0.59 mL, 4.24 mmol) and the resultant solution was added to a solution of 8-fluoro-1H-pyrano[4,3-c]pyridin-1-one hydrochloride (0.50 g, 2.48 mmol) in MeOH (17 mL) with added 4 Å molecular sieves. The reaction mixture was heated at 80° C. for 18 h and then at room temperature for 72 h. The reaction mixture was concentrated in vacuo, the crude residue was treated with EtOAc and the collected organic phases were concentrated in vacuo to give the product (0.26 g, 58%) that was taken to the next step without further purification. UPLC-MS (Acidic Method, 2 min): rt 0.17 min, m/z 181.0 [M+H]$^+$. $^1$H NMR (400 MHz, DMSO-d$_6$): δ ppm 10.75 (s, 1H), 8.52 (d, J=0.9 Hz, 1H), 8.49 (s, 1H), 7.42 (t, J=5.3 Hz, 1H), 6.76 (t, J=5.2 Hz, 1H).

Step 2: 8-(2-Fluoro-4-iodophenylamino)-2-hydroxy-2,6-naphthyridin-1(2H)-one

A solution of 2-fluoro-4-iodoaniline (95 mg, 0.40 mmol) in dry THF (2 mL stirred at −78° C. under N$_2$ was treated with LiHMDS (1M in THF, 1.00 mL, 1.00 mmol) added dropwise. The reaction mixture was stirred for 10 min at −78° C. and then a suspension of 8-fluoro-2-hydroxy-2,6-naphthyridin-1(2H)-one (76 mg, 0.42 mmol) in dry THF (1 mL) was added. The reaction mixture was further stirred at −78° C. for 15 min and then let to warm up to room temperature. After 30 min the reaction mixture was re-cooled down to −78° C. and treated with additional portions of LiHMDS (1M in THF, 1.00 mL, 1.00 mmol) added dropwise. The reaction mixture was further stirred and let to warm up to room temperature then it was quenched with a saturated NH$_4$Cl aqueous solution at 0° C. The aqueous phase was extracted with EtOAc. The combined organic phase was washed with brine, dried over Na$_2$SO$_4$, filtered and concentrated in vacuo at room temperature to give the crude material which was purified by preparative HPLC purification to give the product (9.5 mg, 6%) as a yellow solid. UPLC-MS (Acidic Method, 2 min): rt 1.00 min, m/z 398.0 [M+H]$^+$. $^1$H NMR (400 MHz, DMSO-d$_6$): δ ppm 11.98 (br s, 1H), 10.70 (br s, 1H), 8.43 (s, 1H), 8.30 (s, 1H), 7.84 (d, J=7.5 Hz, 1H), 7.75 (dd, J=10.4, 1.9 Hz, 1H), 7.59-7.46 (m, 2H), 6.72 (d, J=7.5 Hz, 1H).

Example 7: 8-(2-Fluoro-4-iodophenylamino)-2-(2-hydroxyethoxy)-2,6-naphthyridin-1(2H)-one

Step 1: 2-(2-(tert-Butyldiphenylsilyloxy)ethoxy)-8-(2-fluoro-4-iodophenylamino)-2,6-naphthyridin-1(2H)-one To a solution of O-(2-(tert-butyl-diphenylsilyloxy)ethyl) hydroxylamine (0.70 g, 2.22 mmol), Et$_3$N (0.31 mL, 2.22 mmol) and HCl (4N in dioxane, 1.1 mL, 4.44 mmol) in dioxane (5 mL) stirred at room temperature for 15 min was added methyl 3-(2-ethoxyvinyl)-5-fluoroisonicotinate (0.50 g, 2.22 mmol). The reaction mixture was stirred at 50° C. for 18 h. The reaction mixture was cooled down to room temperature, was treated with LiHMDS (1M in THF, 7.1 mL, 7.10 mmol) added dropwise and stirred for 30 min. Then 2-fluoro-4-iodoaniline (0.53 g, 2.22 mmol) was added to the reaction mixture followed by LiHMDS (1M in THF, 2.7 mL, 2.66 mmol) added dropwise and it was further stirred at room temperature. After 45 min an additional portion of LiHMDS (1M in THF, 1.3 mL, 1.33 mmol) was added and the reaction mixture was stirred for 30 min. Then the reaction mixture was quenched with a saturated NH$_4$Cl aqueous solution and extracted with EtOAc. The combined organic phase was washed with brine, dried over Na$_2$SO$_4$, filtered and concentrated in vacuo to give the crude material which was purified by flash column chromatography (Silica, 0-30% EtOAc in hexane+1% Et$_3$N) to give the product (250 mg, 16%) as a yellow glass. UPLC-MS (Acidic Method, 2 min): rt 1.61 min, m/z 680.2 [M+H]$^+$. $^1$H NMR (400 MHz, DMSO-d$_6$): δ ppm 10.45 (s, 1H), 8.42 (s, 1H), 8.30 (d, J=1.3 Hz, 1H), 7.82 (d, J=7.6 Hz, 1H), 7.77 (dd, J=10.4, 1.9 Hz, 1H), 7.65-7.50 (m, 5H), 7.50-7.33 (m, 7H), 6.74 (d, J=7.7 Hz, 1H), 4.49-4.34 (m, 2H), 3.97 (t, J=4.3 Hz, 2H), 0.93 (s, 9H).

Step 2: 8-(2-Fluoro-4-iodophenylamino)-2-(2-hydroxyethoxy)-2,6-naphthyridin-1(2H)-one To a solution of 2-(2-(tert-butyldiphenylsilyloxy)ethoxy)-8-(2-fluoro-4-iodophenylamino)-2,6-naphthyridin-1(2H)-one (250 mg, 0.368 mmol) in THF (5 mL) stirred at room temperature TBAF (1M in THF, 0.37 mL, 0.368 mmol) was added. After 30 min reaction was complete and a saturated NaHCO₃ aqueous solution was added. The mixture was extracted twice with EtOAc, the organic phase was washed with H₂O and brine, dried over Na₂SO₄, filtered and concentrated in vacuo. A half of the crude material was purified by preparative HPLC purification followed by SFC purification to give the product (30 mg, 64%). UPLC-MS (Acidic Method, 2 min): rt 1.03 min, m/z 442.0 [M+H]⁺. $^1$H NMR (400 MHz, DMSO-d₆): δ ppm 10.42 (s, 1H), 8.42 (s, 1H), 8.29 (d, J=1.3 Hz, 1H), 7.86 (d, J=7.6 Hz, 1H), 7.76 (dd, J=10.4, 1.9 Hz, 1H), 7.60-7.53 (m, 1H), 7.49 (t, J=8.5 Hz, 1H), 6.74 (d, J=7.7 Hz, 1H), 4.97 (t, J=5.5 Hz, 1H), 4.28 (dd, J=5.2, 4.1 Hz, 2H), 3.68 (q, J=5.1 Hz, 2H).

Example 8: 8-(2-Fluoro-4-iodophenylamino)-2-isopropoxy-3,4-dihydro-2,6-naphthyridin-1(2H)-one Step 1: Methyl 3-fluoro-5-(2-(isopropoxyimino)ethyl)isonicotinate To a solution of O-isopropylhydroxylamine hydrochloride (495 mg, 4.44 mmol), Et₃N (0.62 mL, 4.44 mmol) and HCl (4N in dioxane, 1.1 mL, 4.44 mmol) in dioxane (8 mL) placed in a pressure tube was added a solution of methyl 3-(2-ethoxyvinyl)-5-fluoroisonicotinate (1.0 g, 4.44 mmol) in dioxane (2 mL). The reaction mixture was sealed and stirred at 50° C. for 18 h. Note: the reaction mixture is in a form of a dense suspension of formed NH₄Cl salt during the process and should be efficiently stirred for best results. Then the reaction mixture was concentrated in vacuo. The crude material was dry loaded on Celite and was purified by flash column chromatography (40 g silica, 0-15% EtOAc in hexanes modified with 1% Et₃N) to give the product (795 mg, 70%, mixture of two isomers) as a pale oil. UPLC-MS (Acidic Method, 2 min): rt 1.07 min, m/z 255.1 [M+H]⁺. $^1$H NMR (400 MHz, DMSO-d₆): δ ppm 8.66 (dd, J=4.0, 1.1 Hz, 2H), 8.53 (s, 1H), 8.49 (s, 1H), 7.47 (t, J=5.4 Hz, 1H), 6.84 (t, J=5.1 Hz, 1H), 4.27 (p, J=6.2 Hz, 1H), 4.15 (p, J=6.2 Hz, 1H), 3.91 (s, 3H), 3.90 (s, 3H), 3.72 (d, J=5.1 Hz, 2H), 3.68 (d, J=5.4 Hz, 2H), 1.17 (d, J=6.2 Hz, 6H), 1.11 (d, J=6.2 Hz, 6H).

Step 2: 8-Fluoro-2-isopropoxy-3,4-dihydro-2,6-naphthyridin-1(2H)-one

To a solution of methyl 3-fluoro-5-(2-(isopropoxyimino)ethyl)isonicotinate (400 mg, 1.575 mmol) in MeOH (4 mL) stirred at room temperature under N₂ flow, with an output to a Drechsel bottle with a solution of bleach and 1M NaOH, NaCNBH₃ (297 mg, 4.724 mmol) was added at once followed by 1M HCl aqueous solution (1.57 mL, 1.575 mmol) added dropwise. The reaction mixture was stirred for 5 days at room temperature. Reaction was quenched with H₂O (50 mL) and extracted with EtOAc (6×25 mL). The organic phase was washed with brine, dried over Na₂SO₄, filtered and concentrated in vacuo to give the product (275 mg, 78%) as a white soft solid used in the next step without further purification. UPLC-MS (Acidic Method, 2 min): rt 0.78 min, m/z 225.1 [M+H]⁺. $^1$H NMR (400 MHz, DMSO-d₆): δ ppm 8.56 (d, J=3.0 Hz, 1H), 8.48 (s, 1H), 4.33 (p, J=6.2 Hz, 1H), 3.82 (t, J=6.6 Hz, 2H), 3.19 (t, J=6.6 Hz, 2H), 1.22 (d, J=6.2 Hz, 6H).

Step 3: 8-(2-Fluoro-4-iodophenylamino)-2-isopropoxy-3,4-dihydro-2,6-naphthyridin-1(2H)-one A solution of 2-fluoro-4-iodoaniline (106 mg, 0.45 mmol) in dry THF (1 mL) stirred at −78° C. under N₂ was treated with LiHMDS (1M in THF, 0.45 mL, 0.45 mmol) added dropwise and the reaction mixture was stirred for 15 min. Then a solution of 2-(cyclopropylmethoxy)-8-fluoro-3,4-dihydro-2,6-naphthyridin-1(2H)-one (100 mg, 0.45 mmol) in dry THF (1 mL) was added and the reaction mixture was further stirred at and let to warm up to room temperature. After 18 h the reaction mixture was re-cooled to −78° C. and LiHMDS (1M in THF, 0.45 mL, 0.45 mmol) was added dropwise and the reaction mixture was further stirred at and let to warm up to room temperature. After 18 h the reaction mixture was quenched with a saturated NH₄Cl aqueous solution (15 mL) and extracted with EtOAc (3×10 mL). The combined organic phase was washed with brine (10 mL), dried over Na₂SO₄, and concentrated in vacuo. The crude material was purified by flash column chromatography (Silica, 0-60% EtOAc in hexanes) to give the product (61 mg, 31%) as an orange gum. UPLC-MS (Acidic Method, 4 min): rt 1.21 min, m/z 442.1 [M+H]⁺. ¹H NMR (400 MHz, DMSO-d₆): δ ppm 10.13 (s, 1H), 8.34 (d, J=1.4 Hz, 1H), 7.98 (s, 1H), 7.73 (dd, J=10.4, 1.9 Hz, 1H), 7.53 (dt, J=8.5, 1.4 Hz, 1H), 7.36 (t, J=8.6 Hz, 1H), 4.36 (p, J=6.2 Hz, 1H), 3.82 (t, J=6.7 Hz, 2H), 3.12 (t, J=6.6 Hz, 2H), 1.24 (d, J=6.2 Hz, 6H).

Example 9: 2-(Cyclopropylmethoxy)-8-(2-fluoro-4-iodophenylamino)-3,4-dihydro-2,6-naphthyridin-1(2H)-one Step 1: Methyl 3-(2-(cyclopropylmethoxyimino)ethyl)-5-fluoroisonicotinate To a solution of O-(cyclopropylmethyl)hydroxylamine hydrochloride (546 mg, 4.44 mmol), Et₃N (0.62 mL, 4.44 mmol) and HCl (4N in dioxane, 1.1 mL, 4.44 mmol) in dioxane (8 mL) placed in a pressure tube was added a solution of methyl 3-(2-ethoxyvinyl)-5-fluoroisonicotinate (1.0 g, 4.44 mmol) in dioxane (2 mL). The reaction mixture was sealed and stirred at 50° C. for 18 h. Note: the reaction mixture is in a form of a dense suspension of formed NH₄Cl salt during the process and should be efficiently stirred for best results. An additional portion of Et₃N (0.62 mL, 4.44 mmol), HCl (4N in dioxane, 1.1 mL, 4.44 mmol) and O-(cyclopropylmethyl)hydroxylamine hydrochloride (273 mg, 2.22 mmol) were added to the reaction mixture stirred at 50° C. in further 30 h. Then the reaction mixture was concentrated in vacuo. The crude material was dry loaded on Celite and was purified by flash column chromatography (45 g silica, 0-10% EtOAc in hexanes modified with 1% Et₃N) to give the product (791 mg, 67%, mixture of two isomers) as a pale oil. UPLC-MS (Acidic Method, 2 min): rt 1.07 min, m/z 267.1 [M+H]⁺. ¹H NMR (400 MHz, DMSO-d₆): δ ppm 8.66 (dd, J=2.4, 1.0 Hz, 2H), 8.54 (s, 1H), 8.50 (s, 1H), 7.52 (t, J=5.4 Hz, 1H), 6.85 (t, J=5.2 Hz, 1H), 3.91 (s, 3H), 3.90 (s, 3H), 3.86 (d, J=7.1 Hz, 2H), 3.76 (d, J=5.2 Hz, 2H), 3.72 (d, J=7.1 Hz, 2H), 3.68 (d, J=5.4 Hz, 2H), 1.14-0.91 (m, 2H), 0.57-0.38 (m, 4H), 0.23 (dt, J=6.1, 4.3 Hz, 2H), 0.18 (dt, J=6.1, 4.3 Hz, 2H).

Step 2: 2-(Cyclopropylmethoxy)-8-fluoro-3,4-dihydro-2,6-naphthyridin-1(2H)-one

To a solution of methyl 3-(2-(cyclopropylmethoxyimino)ethyl)-5-fluoroisonicotinate (600 mg, 2.253 mmol) in MeOH (6 mL) stirred at room temperature under N₂ flow, with an output to a Drechsel bottle with a solution of bleach and 1M NaOH, NaCNBH₃ (425 mg, 6.760 mmol) was added at once followed by 1M HCl aqueous solution (2.25 mL, 2.253 mmol) added dropwise. The reaction mixture was stirred for 5 days at room temperature. Reaction was quenched with H₂O (50 mL) and extracted with EtOAc (6×25 mL). The organic phase was washed with brine, dried over Na₂SO₄, filtered and concentrated in vacuo to give the product (582 mg, 96%) as a light-yellow oil used in the next step without further purification. UPLC-MS (Acidic Method, 2 min): rt 0.81 min, m/z 237.1 [M+H]⁺. ¹H NMR (400 MHz, DMSO-d₆): δ ppm 8.56 (d, J=2.9 Hz, 1H), 8.47 (s, 1H), 3.90 (t, J=6.6 Hz, 2H), 3.82 (d, J=7.3 Hz, 2H), 3.19 (t, J=6.6 Hz, 2H), 1.19-1.03 (m, 1H), 0.55 (dd, J=8.1, 1.9 Hz, 2H), 0.30 (dd, J=4.7, 1.7 Hz, 2H).

Step 3: 2-(Cyclopropylmethoxy)-8-(2-fluoro-4-iodophenylamino)-3,4-dihydro-2,6-naphthyridin-1(2H1)-one A solution of 2-fluoro-4-iodoaniline (201 mg, 0.85 mmol) in dry THF (2 mL) stirred at −78° C. under N₂ was treated with LiHMDS (1M in THF, 0.85 mL, 0.85 mmol) added dropwise and the reaction mixture was stirred for 15 min. Then a solution of 2-(cyclopropylmethoxy)-8-fluoro-3,4-dihydro-2,6-naphthyridin-1(2H)-one (200 mg, 0.85 mmol) in dry THF (2 mL) was added and the reaction mixture was further stirred at and let to warm up to room temperature. After 18 h the reaction mixture was re-cooled to −78° C. and LiHMDS (1M in THF, 0.21 mL, 0.21 mmol) was added dropwise and the reaction mixture was further stirred at and let to warm up to room temperature. After 18 h the reaction mixture was quenched with a saturated NH₄Cl aqueous solution (20 mL) and extracted with EtOAc (3×15 mL). The combined organic phase was washed with brine (20 mL), dried over Na₂SO₄, and concentrated in vacuo. The crude material was purified by flash column chromatography (Silica, 0-60% EtOAc in hexanes) to give the product (132 mg, 34%) as an orange gum. UPLC-MS (Acidic Method, 4 min): rt 1.22 min, m/z 454.1 [M+H]⁺. ¹H NMR (400 MHz, DMSO-d₆): δ ppm 10.11 (s, 1H), 8.34 (s, 1H), 7.98 (s, 1H), 7.73 (dd, J=10.5, 1.9 Hz, 1H), 7.53 (dt, J=8.3, 1.3 Hz, 1H), 7.36 (t, J=8.6 Hz, 1H), 3.90 (t, J=6.8 Hz, 2H), 3.84 (d, J=7.3 Hz, 2H), 3.11 (t, J=6.7 Hz, 2H), 1.20-1.09 (m, 1H), 0.64-0.50 (m, 2H), 0.41-0.23 (m, 2H).

Example 10: 8-(2-Fluoro-4-iodophenylamino)-2-(2-hydroxyethoxy)-3,4-dihydro-2,6-naphthyridin-1(2)-one Step 1: Methyl 3-(9,9-dimethyl-8,8-diphenyl-4,7-dioxa-3-aza-8-siladec-2-enyl)-5-fluoroisonicotinate A solution of methyl 3-(2-ethoxyvinyl)-5-fluoroisonicotinate (1.0 g, 4.44 mmol) in dioxane (10 mL) was treated with HCl (4 N in dioxane, 2.2 mL, 8.88 mmol) and stirred at 45° C. for 18 h. Then the reaction mixture was cooled down to room temperature and a solution of O-(2-(tert-butyl-diphenylsilyloxy)ethyl)hydroxylamine (1.75 g, 5.55 mmol) and Et₃N (0.62 mL, 4.44 mmol) in dioxane (2 mL) was added. The reaction mixture was stirred for 3 days at room temperature and then concentrated in vacuo. The crude material was dry loaded on Celite and was purified by flash column chromatography (80 g silica, 0-10% MeOH in DCM) to give the product (760 mg, 35%, mixture of two isomers) as a light-yellow oil. UPLC-MS (Acidic Method, 4 min): rt 2.65, 2.67 min (two isomers 1:1), m/z 495.2 [M+H]⁺. ¹H NMR (400 MHz, DMSO-d₆): δ ppm 8.66 (dd, J=2.4, 1.0 Hz, 2H), 8.50 (d, J=0.9 Hz, 1H), 8.46 (d, J=0.8 Hz, 1H), 7.68-7.57 (m, 8H), 7.54 (t, J=5.5 Hz, 1H), 7.49-7.33 (m, 12H), 6.90 (t, J=5.2 Hz, 1H), 4.21-4.14 (m, 2H), 4.06-4.00 (m, 2H), 3.85 (s, 3H), 3.88-3.84 (m, 2H), 3.83 (s, 3H), 3.81-3.77 (m, 2H), 3.76 (d, J=5.1 Hz, 2H), 3.66 (d, J=5.5 Hz, 2H), 0.99 (s, 9H), 0.96 (s, 9H).

Step 2: 2-(2-(tert-Butyldiphenylsilyloxy)ethoxy)-8-fluoro-3,4-dihydro-2,6-naphthyridin-1(2H)-one To a solution of methyl 3-(9,9-dimethyl-8,8-diphenyl-4,7-dioxa-3-aza-8-siladec-2-enyl)-5-fluoroisonicotinate (2.82 g, 5.71 mmol) in MeOH (28 mL) stirred at room temperature under N₂ flow, with an output to a Drechsel bottle with a solution of bleach and 1M NaOH, NaCNBH₃ (1.07 g, 17.1 mmol) was added at once followed by 1M HCl aqueous solution (2.86 mL, 2.86 mmol) added dropwise. After 7 h additional portion of 1M HCl aqueous solution (1.43 mL, 1.43 mmol) was added and the reaction mixture was stirred further for 3 days. Reaction was quenched with 1M NaOH aqueous solution and extracted twice with EtOAc. The organic phase was washed with H₂O and brine, dried over Na₂SO₄, filtered and concentrated in vacuo. The crude material was purified by flash column chromatography (Silica, 20-50% EtOAc in heptane) to give the product (1.90 g, 72%) as a light-yellow solid. UPLC-MS (Acidic Method, 2 min): rt 1.37 min, m/z 465.0 [M+H]⁺. ¹H NMR (400 MHz, DMSO-d$_6$): δ ppm 8.56 (d, J=2.9 Hz, 1H), 8.46 (s, 1H), 7.71-7.60 (m, 4H), 7.51-7.33 (m, 6H), 4.15 (dd, J=5.5, 4.0 Hz, 2H), 3.93-3.83 (m, 4H), 3.16 (t, J=6.6 Hz, 2H), 1.00 (s, 9H).

Step 3: 2-(2-(tert-Butyldiphenylsilyloxy)ethoxy)-8-(2-fluoro-4-iodophenylamino)-3,4-dihydro-2,6-naphthyridin-1(2H)-one To a solution of 2-fluoro-4-iodoaniline (512 mg, 2.16 mmol) in THF (2.5 mL) stirred at room temperature LiHMDS (1M in THF, 2.6 mL, 2.59 mmol) was added. The mixture was stirred for 15 min and then added dropwise to a solution of 2-(2-(tert-butyldiphenylsilyloxy)ethoxy)-8-fluoro-3,4-dihydro-2,6-naphthyridin-1(2H)-one (536 mg, 1.08 mmol) in THF (2.5 mL) stirred at room temperature. The reaction mixture was stirred for 18 h at room temperature. The reaction was then quenched with a saturated NH$_4$Cl aqueous solution and extracted twice with EtOAc. The organic phase was washed with brine, dried over Na$_2$SO$_4$, filtered and concentrated in vacuo. The crude material was purified by flash column chromatography (Silica, 10-40% EtOAc in heptane) to give the product (316 mg, 43%). UPLC-MS (Acidic Method, 2 min): rt 1.58 min, m/z 682.0 [M+H]$^+$. $^1$H NMR (400 MHz, DMSO-d$_6$): δ ppm 10.10 (s, 1H), 8.35 (d, J=1.4 Hz, 1H), 7.97 (s, 1H), 7.73 (dd, J=10.4, 2.0 Hz, 1H), 7.68-7.62 (m, 4H), 7.53 (ddd, J=8.4, 2.0, 0.9 Hz, 1H), 7.49-7.39 (m, 6H), 7.35 (t, J=8.6 Hz, 1H), 4.21-4.13 (m, 2H), 3.95-3.85 (m, 4H), 3.09 (t, J=6.7 Hz, 2H), 1.00 (s, 9H).

Step 4: 8-(2-Fluoro-4-iodophenylamino)-2-(2-hydroxyethoxy)-3,4-dihydro-2,6-naphthyridin-1(2H)-one To a solution of 2-(2-(tert-butyldiphenylsilyloxy)ethoxy)-8-(2-fluoro-4-iodophenylamino)-3,4-dihydro-2,6-naphthyridin-1(2H)-one (360 mg, 0.530 mmol) in THF (4 mL) stirred at room temperature TBAF (1M in THF, 0.53 mL, 0.530 mmol) was added. After 10 min reaction was complete and a saturated NaHCO$_3$ aqueous solution was added. The mixture was extracted twice with EtOAc, the organic phase was washed with H$_2$O and brine, dried over Na$_2$SO$_4$, filtered and concentrated in vacuo. A half of the crude material (200 mg) was purified by preparative HPLC purification to give the product (75.8 mg, 64%) as a yellow solid. UPLC-MS (Acidic Method, 2 min): rt 0.99 min, m/z 444.0 [M+H]$^+$. $^1$H NMR (400 MHz, DMSO-d$_6$): δ ppm 10.07 (s, 1H), 8.34 (d, J=1.4 Hz, 1H), 7.98 (s, 1H), 7.73 (dd, J=10.5, 2.0 Hz, 1H), 7.54 (dt, J=8.4, 1.4 Hz, 1H), 7.36 (t, J=8.6 Hz, 1H), 4.80 (t, J=5.5 Hz, 1H), 4.05 (dd, J=5.8, 3.9 Hz, 2H), 3.90 (t, J=6.7 Hz, 2H), 3.63 (q, J=5.1 Hz, 2H), 3.12 (t, J=6.7 Hz, 2H).

Example 11: 2-ethoxy-8-((2-fluoro-4-iodophenyl)amino)-3,4-dihydro-2,6-naphthyridin-1(2H)-one Compound 1.011 can be prepared as described in Example 8, replacing the 0-isopropylhydroxylamine hydrochloride in Step 1 with an appropriate O-ethylhydroxylamine which is commercially available or prepared using conditions known to one of ordinary skill in the art.

| Comp. No. | Structure |
|---|---|
| 1.011 | 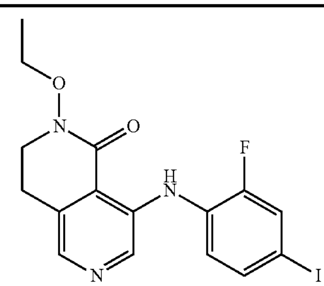 |

Example 12: 8-((2-Fluoro-4-iodophenyl)amino)-3,4-dihydro-2,6-naphthyridin-1(2H)-one A solution of 2-ethoxy-8-(2-fluoro-4-iodophenylamino)-3,4-dihydro-2,6-naphthyridin-1(2H)-one (40 mg, 93.6 µmol) in dry THF (1.1 mL) stirred at room temperature under N$_2$ was treated with SmI$_2$ (0.1M in THF, 3.74 mL, 0.374 mmol) added dropwise and the reaction mixture was stirred for 5 min. Then the reaction mixture was quenched with a saturated Na$_2$S$_2$O$_4$ aqueous solution (10 mL) and extracted with EtOAc (3×10 mL). The combined organic phase was washed with brine, dried over Na$_2$SO$_4$, and concentrated in vacuo. The crude material (31.4 mg) was purified by preparative HPLC purification to give the product (8.1 mg, 23%) as a yellow solid.

Alternatively, a solution of 2-(cyclopropylmethoxy)-8-(2-fluoro-4-iodophenylamino)-3,4-dihydro-2,6-naphthyridin-1(2H)-one (40 mg, 88.2 µmol) in dry THF (1.1 mL) stirred at room temperature under N₂ was treated with SmI₂ (0.1M in THF, 3.74 mL, 0.374 mmol) added dropwise and the reaction mixture was stirred for 5 min. Then the reaction mixture was quenched with a saturated Na₂S₂O₄ aqueous solution (10 mL) and extracted with EtOAc (3×10 mL). The combined organic phase was washed with brine, dried over Na₂SO₄, and concentrated in vacuo. The crude material (31.6 mg) was purified by preparative HPLC purification to give the product (14.6 mg, 43%) as a yellow solid.

UPLC-MS (Acidic Method, 2 min): rt 1.00 min, m/z 383.9 [M+H]⁺. ¹H NMR (400 MHz, DMSO-d₆) δ ppm 10.30 (s, 1H), 8.50 (br s, 1H), 8.40 (s, 1H), 8.00 (s, 1H), 7.71 (dd, J=10.5, 2.0 Hz, 1H), 7.51 (dd, J=8.4, 1.7 Hz, 1H), 7.37 (t, J=8.6 Hz, 1H), 3.41 (td, J=6.6, 2.8 Hz, 2H), 2.87 (t, J=6.6 Hz, 2H).

The following compounds can be prepared as described in Example 10, replacing the 2-fluoro-4-iodoaniline in Step-3 with an appropriate aniline which is commercially available or prepared using conditions known to one of ordinary skill in the art.

| Comp. No. | Structure |
|---|---|
| 1.019 | (structure) |
| 1.020 | (structure) |

The following compounds can be prepared as follows: 1) as described in Step 1 of Example 10, replacing the O-(2-(tert-butyl-diphenylsilyloxy)ethyl)hydroxylamine with an appropriate hydroxylamine which is commercially available or prepared using conditions known to one of ordinary skill in the art; 2) as described in Step 2 of Example 4 for the hydrolysis of the ester; and 3) as described in Step 3 of Example 4 for the coupling reaction with 2-fluoro-4-iodoaniline.

| Comp. No. | Structure |
|---|---|
| 1.013 | (structure) |
| 1.016 | (structure) |

The following compounds can be prepared as described in Example 5 by esterification.

| Comp. No. | Structure |
|---|---|
| 1.014 | (structure) |
| 1.017 | (structure) |

The following compounds can be prepared from the corresponding acid (e.g., Compound Nos. 1.013 and 1.016 with hydroxylamine by amidation using conditions known to one of ordinary skill in the art.

| Comp. No. | Structure |
|---|---|
| 1.015 | (structure) |
| 1.018 | (structure) |

The following compounds can be prepared as follows: 1) as described in Step 1 of Example 10, replacing the O-(2-(tert-butyl-diphenylsilyloxy)ethyl)hydroxylamine with an appropriate (2,2-dimethyl-1,3-dioxolan-4-yl)methanamine which is commercially available or prepared using conditions known to one of ordinary skill in the art.

| Comp. No. | Structure |
|---|---|
| 1.022 | (structure) |
| 1.023 | (structure) |

Example 13: MEK Inhibition Assay-1

The following procedure can be used to measure biochemical activity. MEK1 inhibitory activity of compounds were tested using the following procedure. See Anastassiadis T, et al. *Comprehensive assay of kinase catalytic activity reveals features of kinase inhibitor selectivity. Nat Biotechnol.* 2011, 29(11), 1039-45.

Reagents:
  Reaction buffer: 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO
  Enzyme: MEK1, Invitrogen cat #PV3303
  N-terminal His-tagged recombinant human full length protein, expressed in insect cells. Activated in vitro by RAF1. MW=49.2 kDa, GenBank Accession No. NP_002746.
  Substrate: 5 µM ERK2 (K52R),
  Kinase-dead mutant, (GenBank Accession No. NM_0011949), aa2-358 with N-terminal His6 tag, MW=43.63 kDa, expressed in *E. coli*.

The substrate was prepared in freshly prepared Reaction Buffer. The kinase was delivered into the substrate solution and gently mixed. Test compounds were delivered in 100% DMSO into the kinase reaction mixture by Acoustic technology (Echo550; nanolitter range), and incubated for 20 min at room temperature. $^{33}$P-ATP was delivered into the reaction mixture to initiate the reaction. The reaction mixture was incubated for 2 hours at room temperature. Kinase activity was detected by P81 filter-binding method.

Example 14: MEK Inhibition Assay-2

MEK1 inhibitory activity of compounds were tested using the following procedure (protocol available at thermofisher.com/content/dam/LifeTech/migration/files/drug-discovery/pdfs.par.60256.file.dat/20130430%20ssbk%20customer%20protocol%20and%20assay%20conditions.pdf). The Z'-LYTE biochemical assay (ThermoFisher) employs a fluorescence-based, coupled-enzyme format and is based on the differential sensitivity of phosphorylated and non-phosphorylated peptides to proteolytic cleavage.

Test compounds in 100% DMSO were screened in 1% DMSO (final) in the well. For 10 point titrations, 3-fold serial dilutions are conducted from the starting concentration of 30 µM.

The peptide/kinase, MAP2K1 (MEK1)/inactive MAPK1 (ERK2)/Ser/Thr 03, mixture ("Peptide/kinase Mixture") was diluted to a 2× working concentration in the following buffer ("Kinase Buffer"): 50 mM HEPES pH 7.5, 0.01% BRIJ-35, 10 mM MgCl2, 1 mM EGTA. The final 10 µL kinase reaction consisted of 0.06-0.25 ng MAP2K1 (MEK1), 105 ng inactive MAPK1 (ERK2), and 2 µM Ser/Thr 03 in 50 mM HEPES pH 7.5, 0.01% BRIJ-35, 10 mM MgCl$_2$, 1 mM EGTA. After the 1 hour incubation, 5 µL of a 1:1024 dilution of Development Reagent A (available from Invitrogen, catalog no. PV3295) was added.

ATP solutions were diluted to a 4× working concentration in Kinase Buffer (50 mM HEPES pH 7.5, 0.01% BRIJ-35, 10 mM MgCl$_2$, 1 mM EGTA). ATP Km apparent was previously determined using a Z'-LYTE assay. The Development Reagent was diluted in Development Buffer (available from Invitrogen, catalog no. P3127).

Assay Protocol: 2.5 µL of 4× test compound or 100 nL of 100× Test Compound plus 2.4 µL Kinase Buffer, 5 µL of the 2× Peptide/Kinase Mixture, 2.5 µL of 4×ATP Solution were added to the plates and placed on a shake plate for 30-seconds. The kinase reaction was allowed to proceed for 60-minute at room temperature, before 5 µL of Development Reagent Solution was added, and the mixture agitated for 30-seconds on a shake plate. The mixture was incubated for 60-minute at room temperature. Fluorescence was measured using a plate reader and the data were analyzed.

The maximum emission ratio was established by the 0% Phosphorylation Control (100% Inhibition Control), which contained no ATP and therefore exhibited no kinase activity. This control yielded 100% cleaved peptide in the Development Reaction. The 100% Phosphorylation Control, which consisted of a synthetically phosphorylated peptide of the same sequence as the peptide substrate, was designed to allow for the calculation of percent phosphorylation. This control yielded a very low percentage of cleaved peptide in the Development Reaction. The 0% Phosphorylation and 100% Phosphorylation Controls allow for the calculation of the percent phosphorylation achieved in a specific reaction well. Control wells did not include any kinase inhibitors.

The minimum emission ratio in a screen was established by the 0% Inhibition Control, which contained active kinase. This control was designed to produce a 10-50% phosphorylated peptide in the Kinase Reaction. Cascade assays may produce up to 70% phosphorylated peptide.

A known inhibitor control standard curve, 10 point titration, was run for each individual kinase on the same plate as the kinase to ensure the kinase was inhibited within an expected IC$_{50}$ range previously determined.

The following controls are prepared for each concentration of Test Compound assayed. The Development Reaction Interference was established by comparing the Test Compound Control wells that did not contain ATP versus the 0% Phosphorylation Control (which did not contain the Test Compound). The expected value for a non-interfering compound should be 100%. Any value outside of 90% to 110% was flagged. The Test Compound Fluorescence Interference was determined by comparing the Test Compound Control wells that did not contain the Kinase/Peptide Mixture (zero peptide control) versus the 0% Inhibition Control. The expected value for a non-fluorescence compound should be 0%. Any value>20% was flagged.

The data in Table A was calculated. XLfit from IDBS was used. The dose response curve was curve fit to model number 205 (sigmoidal dose-response model). If the bottom of the curve did not fit between −20% & 20% inhibition, it was set to 0% inhibition. If the top of the curve did not fit between 70% and 130% inhibition, it was set to 100% inhibition.

TABLE A

| | Equation |
|---|---|
| Correction for Background Fluorescence | $FI_{Sample} - FI_{TCFICtl}$ |
| Emission Ratio (using values corrected for background fluorescence) | $\dfrac{\text{Coumarin Emission (445 nm)}}{\text{Fluorescein Emission (520 nm)}}$ |
| % Phosphorylation (% Phos) | $\left\{1 - \dfrac{(\text{Emission Ratio} \times F_{100\%}) - C_{100\%}}{(C_{0\%} - C_{100\%}) + [\text{Emission Ratio} \times (F_{100\%} - F_{0\%})]}\right\} \div 100$ |
| % Inhibition | $\left\{1 - \dfrac{\% \text{Phos}_{Sample}}{\% \text{Phos}_{0\%InhibitionCtl}}\right\} \div 100$ |
| Z (using Emission Ratio values) | $1 - \dfrac{3 \div \text{Stdev}_{0\%PhosCtl} + 3 \div \text{Stdev}_{0\%Inhibition}}{\text{Mean}_{0\%PhosCtl} - \text{Mean}_{0\%Inhibition}}$ |
| Difference Between Data Points (single point only) | $|\% \text{Inhibition}_{Point1} - \% \text{Inhibition}_{Point2}|$ |
| Development Reaction Interference (DRI) (no ATP control) | $\dfrac{\text{Emission Ratio}_{DRICtl}}{\text{Emission Ratio}_{0\%PhosCtl}}$ |
| Test Compound Fluorescence Interference (TCFI) (check both Coumarin and Fluorescein emissions) | $\dfrac{FI_{TCFICtl}}{FI_{0\%InhibitorCtl}}$ |

FI = Fluorescence Intensity
$C_{100\%}$ = Average Coumarin emission signal of the 100% Phos. Control
$C_{0\%}$ = Average Coumarin emission signal of the 0% Phos. Control
$F_{100\%}$ = Average Fluorescein emission signal of the 100% Phos. Control
$F_{0\%}$ = Average Fluorescein emission signal of the 0% Phos. Control
DRI = Development Reaction Interference
TCFI = Test Compound Fluorescence Interference Table 3 lists the MEK1 inhibition assay results of selected compounds according to the above procedure. A indicates an $IC_{50}$ of less than or equal to 150 nM, B indicates an $IC_{50}$ of greater than 150 nM and less than or equal to 1.5 µM, and C indicates an $IC_{50}$ of greater than 1.5 µM.

TABLE 3

MEK1 Inhibition Assay Results

| Compound No. | $IC_{50}$ against MEK1 |
|---|---|
| 1.001 | A |
| 1.002 | A |
| 1.003 | B |
| 1.004 | C |
| 1.005 | C |
| 1.006 | B |
| 1.007 | B |
| 1.008 | ND |
| 1.009 | ND |
| 1.010 | B |
| 1.011 | B |
| 1.012 | B |

ND not determined

Example 15: Cell-Based Assay-1

Preparation of cell lines useful for testing the soft MEK inhibitors in NF1 related cell-proliferation assays can be found in Basu et al. Nature 356: 713-715, 1992; and DeClue et al. Cell 69: 265-273, 1992. In addition, exemplary in vitro and in vivo models to determine efficacy of the soft MEK inhibitors described herein can be found in U.S. Pat. Nos. 8,211,875 and 8,487,004, which are incorporated by reference in their entireties.

Example 16: Cell-Based Assay-2

Alternatively, the following procedure can be used to measure cell-based activity. Test compounds were dissolved in DMSO in 10 mM stock. Cell Titer-Glo® 2.0 Luminescent cell viability assay reagent was purchased from Promega (Madison, WI). A375 and HCT116 cell lines were purchased from American Type Culture Collection (Manassas, VA). For A375 cells, cell culture media was DMEM+10% FBS. Cell culture media are listed in the following table. For HCT116 cells, cell culture media was McCoy's 5A+10% FBS. All media were supplemented with 100 µg/mL of penicillin, and 100 µg/mL of streptomycin. Cultures were maintained at 37° C. in a humidified atmosphere of 5% $CO_2$ and 95% air.

Test compounds were diluted in DMSO solution with 10-dose and 3-fold dilutions in a source plate starting at 10 mM. 25 nL of each test compound was delivered from the source plate to each well of the 384-well cell culture plates (T=Final) by Echo 550. 25 µL of culture medium containing 2000 of A375 or HCT116 cells was added to each of the wells in duplicates of the cell culture plates (T=0 and T=Final). 25 µL of Cell Titer Glo 2.0 reagent was added to each well of cell culture plate (T=0). The contents were mixed on an orbital shaker for 2 min and incubated at room temperature for 15 min to stabilize luminescent signal. Luminescence was recorded by Envision 2104 Multilabel Reader (PerkinElmer, Santa Clara, CA). The number of viable cells in culture was determined based on quantitation of the ATP present in each culture well. The cells in cell culture plate (T=Final) were incubated with the compounds at 37° C., 5% $CO_2$ for 72 hours. 25 µL of Cell Titer Glo 2.0 reagent was added to each well. The contents were mixed on an orbital shaker for 2 min and incubated at room temperature for 15 min to stabilize luminescent signal. Luminescence was recorded by Envision 2104 Multilabel Reader (PerkinElmer, Santa Clara, CA). The number of viable cells in culture was determined based on quantitation of the ATP present in each culture well. The $GI_{50}$ curves were plotted using the GraphPad Prism 4 program based on a sigmoidal dose-response equation Y=Bottom+(Top−Bottom)/(1+10^((Log EC50−X)*HillSlope)). All parameters in the equation were calculated by GraphPad Prism 4 program. $GI_{50}$ is the concentration of the compound calculated according to $[(T_i-T_z)/(C-T_z)]*100=50$ where $T_i$ is the row data of cells with test compounds at T=Final; $T_z$ is the row data of cells without compounds at T=0 h; C is the row data of cells with control compound staurosporine (Sigma-Aldrich) at T=72 h. Accordingly, $GI_{50}$ is the value of $10^X$, where X was calculated by the Curve Fitting Equation when Y=50 using Excel.

Example 17: S9 Stability Assays

Compounds can be assessed for metabolic stability in human skin by assessing their rate of disappearance from human S9 skin fraction. Similarly, compounds can be assessed for metabolic stability in human liver by assessing their rate of disappearance from human S9 liver fraction. The protocol below is used to assess the difference between skin and hepatic metabolism.

The assay was carried out in 96-well microtiter plates at 37° C. Reaction mixtures (25 µL) contained a final concentration of 1 µM test compound, 2 mg/mL liver or skin protein, and 1 mM NADPH in buffer (100 mM potassium phosphate, pH 7.4 buffer with 1 mM EDTA, 3 mM $MgCl_2$). At each of the time points (0, 15, 30, and 60 minutes), 150 µL of quench solution (100% acetonitrile with 0.1% formic acid) with internal standard was transferred to each well. Besides the zero minute controls, mixtures containing the same components except the NADPH were also prepared as the negative control. Verapamil or testosterone was included as a positive control to verify assay performance. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min control reaction incubations. Initial rates were calculated for the compound concentration and used to determine $t_{1/2}$ values and subsequently, the intrinsic clearance, $CL_{int}$= (0.693) (1/$t_{1/2}$ (min)) (mL incubation/mg of S9 protein).

Table 4 lists $t_{1/2}$ values for the above liver S9 stability assay. "A" indicates a half life of greater than 50 minutes and less than or equal to 200 minutes and "B" indicates a half life of less than or equal to 50 minutes.

TABLE 4

Human Liver S9
Fraction Stability Results

| Compound No. | Liver S9 fraction stability, $t_{1/2}$ (min) |
|---|---|
| 1.007 | A |
| 1.010 | A |
| 1.012 | B |

Example 18: Microsomal Stability Assay

Metabolic stability of testing compound can be evaluated using human liver microsomes to predict intrinsic clearance. Human liver microsomes are obtained from Corning Gentest.

The assay was carried out in 96-well microtiter plates at 37° C. Reaction mixtures (25 µL) contain a final concentration of 1 µM test compound, 0.5 mg/mL liver microsomes protein, and 1 mM NADPH in buffer (100 mM potassium phosphate, pH 7.4 buffer with 3 mM $MgCl_2$). At each of the time points (0, 15, 30, and 60 minutes), 150 µL of quench solution (100% acetonitrile with 0.1% formic acid) with internal standard was transferred to each well. Verapamil was included as a positive control to verify assay performance. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min time incubation. Initial rates were calculated for the compound concentration and used to determine $t_{1/2}$ values and subsequently, the intrinsic clearance, $CL_{int}=(0.693)(1/t_{1/2}$ (min))(g of liver/kg of body weight)(mL incubation/mg of microsomal protein)(45 mg of microsomal protein/g of liver weight).

Example 19: In Vivo Model

Study Procedures: A topical formulation of a compound described herein along with a topical formulation of vehicle are applied to the skin of nude mice in duplicate. Skin is biopsied at discrete time intervals and bisected with half snap frozen in liquid nitrogen and half formalin fixed and paraffin embedded. Protein is isolated for Western blot analysis for p-ERK levels.

p-ERK immunostaining is performed of FFPE sections for cell-specific analysis of p-ERK levels. Additional analysis includes H&E staining to investigate skin integrity.

A compound is assessed in suppressing p-ERK, a downstream biomarker of RAS/MAPK signaling in murine skin. In addition, proliferation of murine skin, apoptosis in murine skin, and histologic integrity of murine skin are also assessed.

Mice: 8 week old 129 mice obtained from Jackson laboratories are shaved prior to start of study. Approximately 21 mice were used for study. A compound is applied to the hairless dorsal skin of the mouse and at 12 hour intervals and skin biopsies are obtained prior to treatment, 24 hours, 72 hours and at 96 hours using 6 mm punch biopsies.

Western Blot analysis: For immunoblotting, epidermal skin is snap frozen in liquid nitrogen immediately after biopsy. The epidermis is lysed in lysis buffer and run on Western blots. Antibodies used for immunoblotting include rabbit anti-phospho-p44/42 MAPK (1:3000, Cell Signaling) and rabbit anti-p44/42 MAPK (1:3000, Cell Signaling), mouse anti-actin (1:5,000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 µm paraffin sections. Antigen retrieval is accomplished with enzyme treatment (1:1000) using standard protocols. Antibodies used are rabbit p-ERK (Cell Signaling, 4307S, 1:100). Bond Polymer Refine anti-rabbit HRP Detection (Leica Biosystems) is used according to manufacturer's protocol. Sections are then counterstained with hematoxylin, dehydrated and film coverslipped using a TissueTek-Prisma and Coverslipper (Sakura).

Histologic analysis: H&E is performed on 5 µM paraffin sections and tissue is examined to assess for cellular toxicity, inflammation or other changes in the integrity of murine skin.

Exogenous RAS activation in murine skin: The experiments are to be conducted in untreated murine skin. Alternatively, skin is pre-treated with TPA to enhance p-ERK levels. TPA-induced RAS/MAPK activation is performed with 96 hours of 12.5 uG TPA in 100 µL acetone to the skin of nude mice. Studies are performed 48 hours after TPA exposure.

T-test is used to assess differences in p-ERK and Ki-67 in samples treated with topical MEK1 inhibitors compared to vehicle control.

Example 20: In Vivo Mouse Model

A compound described herein is tested in a mouse model of NF1, e.g., genetically modified mouse model of NF1, a human dermal neurofibroma xenograft to nude mouse model or both. For example, methods using the $Nf1^{flox/flox}$; Dhh-Cre mouse model described in Jousma et al. Pediatr. Blood Cancer 62: 1709-1716, 2015 are used in this study. Magnetic resonance imaging (MRI) and volumetric measurements is used to measure tumor volumes.

Example 21: Human Dermal Neurofibroma Explant Protocol

Dermal neurofibromas (or cutaneous neurofibromas) are benign tumors which develop in individuals affected with Neurofibromatosis-1 (NF1), a rare genetic disease caused by mutations in the NF1 gene, leading to downstream activation of the RAS/MAPK pathway. Recent studies have demonstrated that inhibition of MEK1 using systemic MEK inhibitors can suppress neurofibromas and other NF-1 related tumors in murine models. See, for example, *New Engl J Med* 2016, 375; 26; *J Clin Invest.* 2013, 123(1), 340-347; and *Pediatr Blood Cancer* 2015, 62(10), 1709-1716. This study establishes an in vitro neurofibroma explant model.

Study Objectives: The primary objective is to assess the efficacy of a topically-formulated compound described herein in suppressing p-ERK, a downstream biomarker of RAS/MAPK signaling in neurofibroma explants. The secondary objectives is to assess permeability (where the compound was applied topically) of neurofibroma explants treated with a compound described herein.

Protocol-1:

Sample Collection and Eligibility: Primary dermal neurofibromas or cutaneous neurofibromas are obtained from patients with clinical or genetic diagnoses of NF1. Discarded human neurofibromas samples are obtained from the Stanford Surgery Clinic, using an approved human subjects protocol (Stanford IRB #18325). Specimens are identified under the direction of the Principal Investigator and placed in cell proliferation media (DMEM/F12 containing penicillin/streptomycin (0.1%); fungizone (40 µg/mL); B27 (without vitamin A).

Patients have the following data to be enrolled in the study: Patient is older than 18 years of age; patient is not undergoing chemotherapy treatment at time of biopsy; and patients met clinical and/or genetic diagnosis of NF1based on presence of two of the following:

1. Six or more café-au-lait macules over 5 mm in diameter in prepubertal individuals and over 15 mm in greatest diameter in postpubertal individuals.
2. Two or more neurofibromas of any type or one plexiform neurofibroma.
3. Freckling in the axillary or inguinal regions.
4. Two or more Lisch nodules (iris hamartomas).
5. Optic glioma.
6. A distinctive osseous lesion such as sphenoid dysplasia or thinning of long bone cortex, with or without pseudarthrosis.
7. First-degree relative (parent, sibling, or offspring) with NF-1 by the above criteria.

Study procedures: Samples are primary, untreated neurofibromas of at least 6 mm in size; samples are excised by a shave, punch biopsy or elliptical excision; samples have a histologic diagnosis of dermal neurofibroma or cutaneous neurofibroma. Specimens are identified under the direction of the Principal Investigator Specimens are chopped into 2 mm fragments and placed in 24-well plates containing cell proliferation media (DMEM/F12 containing penicillin/streptomycin (0.1%); fungizone (40 µg/mL); B27 (without vitamin A) and submerged in media with drug. For topical gel application, samples are placed in 96 well plates with epidermal surface exposed to air.

Western Blot analysis: For immunoblotting, total skin biopies are lysed in lysis buffer and run on Western blots. Antibodies used for immunoblotting includ rabbit anti-phospho-p44/42 MAPK (1:3000, Cell Signaling) and rabbit anti-p44/42 MAPK (1:3000, Cell Signaling), rabbit anti-phospho-Mek1/2 (1:3000, Cell Signaling), mouse anti-actin (1:5000, Sigma-Aldrich), donkey anti-mouse IgG conjugated to horseradish peroxidase (HRP; 1:40,000, Amersham Biosciences) and goat anti-rabbit IgG conjugated HRP (1:40,000, Jackson ImmunoResearch).

Immunohistochemistry: Immunohistochemistry is performed on 5 µm paraffin sections. Antigen retrieval is accomplished with enzyme treatment (1:1000) using standard protocols. Antibodies used are rabbit p-ERK (Cell Signaling, 4307S, 1:100). Bond Polymer Refine anti-rabbit HRP Detection (Leica Biosystems) is used according to manufacturer's protocol. Sections are then counterstained with hematoxylin, dehydrated and film coverslipped using a TissueTek-Prisma and Coverslipper (Sakura).

Data Analysis: Semi-quantitative Western blot is used to assess differences in p-ERK in samples treated with a compound described herein compared to vehicle control.

Study Management: The study is conducted with oversight from an IRB with patient informed consent and HIPAA authorization.

Protocol-2:

Explant Protocol: Human cutaneous neurofibroma explant samples are collected in DMEM/F-12 (Thermo Fisher, Cat #11320033) supplemented with 1×B27 supplement (Thermo Fisher, Cat #17504044), 2.5 µg/ml of Amphotericin B (Thermo Fisher, Cat #15290018), and 50 units/ml of Penicillin-50 µg/ml of Streptomycin (Thermo Fisher, Cat #15070063) and incubated in the same medium for subsequent treatment. The specimen is cut into small cubes containing both the epidermis and dermis. The tissues are partially submerged in the medium in 384-well plate with the epidermis exposed to the air.

The tissues are fully submerged in the medium in 48-well plate and 5 µl of compounds dissolved in DMSO were added to 200 µl of the medium in each well. After 4 h incubation at 37° C. and 5% $CO_2$, the tissues are harvested and half of the specimen is flash frozen in liquid nitrogen for Western Blot analysis. The other half of the specimen is fixed for 24 hours in 10% formalin and then transferred to 70% ethanol for Western Blot analysis.

Skin samples are thawed on ice and weighed. 10 volume (10 µl for each mg of tissue) of lysis buffer (RIPA buffer+0.5 mM EDTA+1×Halt protease and phosphatase inhibitor cocktail) is then added to each sample. The samples are cut into smaller pieces and homogenized with a sonicating probe on ice. The homogenized samples are centrifuged at 12,000 rpm 4° C. for 10 minutes. Supernatant is transferred to a new tube and stored at −80° C. until Western Blot analysis.

Western Blot analysis: The lysate is thawed on ice and protein concentration is determined by the BCA protein assay kit using bovine serum albumin (BSA) as standards. All samples are diluted with lysis buffer to reach the same final concentration. 10-20 µg of total protein is loaded to each well and separated on a NuPAGE 4-12% Bis-Tris gel (Thermo Fisher) in 1× NuPAGE MES SDS running buffer (Thermo Fisher, Cat #NP0002). Proteins are then transferred to a PVDF membrane. The membrane is then blocked for 1 hour in 1×TBST (Tris buffered saline+0.1% Tween 20) with either 5% non-fat milk (for total ERK) or 5% BSA (for phospho-ERK and α-tubulin). The following primary antibodies are used (diluted in the same blocking solution): monoclonal rabbit anti-phospho-p44/42 MAPK (Erk1/2) (Thr202/Tyr204) antibody (Cell Signaling, Cat #4370L) at 1:3000, monoclonal rabbit anti-p44/42 MAPK (Erk1/2) antibody (Cell Signaling, Cat #4695S) at 1:3000, monoclonal mouse anti-α-tubulin (DM1A) antibody (Cell Signaling, Cat #3873S) at 1:3000-1:4000. The membrane is incubated with the primary antibodies overnight at 4° C. followed by three washes with 1×TBST. Secondary antibodies goat anti-rabbit IgG (H+L), HRP (Thermo Fisher, Cat #31460) and peroxidase-conjugated affinipure goat anti-mouse IgG (H+L) (Jackson Immuno Research, Cat #115-035-062) are diluted in 1×TBST with 2% non-fat milk for total ERK and or 2% BSA for phospho-ERK and α-tubulin with the same concentration of primary antibodies and incubated for 1-3 hours at room temperature. After three washes with 1×TBST, the blots are developed with either WesternBright ECL HRP substrate (Advansta, Cat #K12045-D50).

Immunohistochemistry: Antigen retrieval is accomplished with enzymatic treatment. Sections are blocked with 10% normal goat serum and subsequently incubated in phospho-p44/42 MAPK (Erk1/2) rabbit monoclonal antibody (Cell Signaling) or mouse anti-Ki-67 (Pharmingen) at 1:100 dilution for 60 minutes at room temperature. Detection is achieved with a peroxidase-conjugated anti-rabbit system (Leica Biosystem).

Data Analysis: Semi-quantitative Western blot is used to assess differences in p-ERK in samples treated with a compound described herein compared to vehicle control.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula (I):

(I)

or a stereoisomer, mixture of stereoisomers, or a pharmaceutically acceptable salt thereof, wherein:
subscript n is an integer from 0 to 2;
bond "a" is a single or double bond;
$R^1$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl) amino-$C_1$-$C_6$ alkyl, heterocycloalkyl, heterocycloalkyl-$C_1$-$C_6$ alkyl, $R^5$—C(O)—$C_1$-$C_6$ alkyl, or —OR$^4$, wherein each of the $C_3$-$C_8$ cycloalkyl and heterocycloalkyl groups is unsubstituted or substituted with one to six $R^6$;
$R^2$ is halo, $C_1$-$C_6$ alkyl, —S—$C_1$-$C_6$ alkyl, $C_3$-$C_8$ cycloalkyl, $C_2$-$C_6$ alkenyl, or $C_2$-$C_6$ alkynyl;
$R^{2a}$ is halo or $C_1$-$C_6$ alkyl;
each $R^3$ is independently halo or $C_1$-$C_6$ alkyl;
$R^{3a}$ and $R^{3b}$ are each independently hydrogen, halo, $C_1$-$C_6$ alkyl, $C_2$-$C_6$ alkenyl, or $C_2$-$C_6$ alkynyl;
$R^4$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl) amino-$C_1$-$C_6$ alkyl, heterocycloalkyl, heterocycloalkyl-$C_1$-$C_6$ alkyl, or $R^5$—C(O)—$C_1$-$C_6$ alkyl, wherein each of the $C_3$-$C_8$ cycloalkyl and heterocycloalkyl groups is unsubstituted or substituted with one to six $R^6$;
$R^5$ is hydroxy, $C_1$-$C_6$ alkoxy, amino, $C_1$-$C_6$ alkylamino, di-($C_1$-$C_6$ alkyl) amino, hydroxyamino, or N—$C_1$-$C_6$ alkyl hydroxyamino; and
each $R^6$ is independently halo, hydroxy, oxo, $C_1$-$C_6$ alkyl, $C_3$-$C_8$ cycloalkyl, $C_1$-$C_6$ alkoxy, $C_1$-$C_6$-hydroxyalkyl, $C_1$-$C_6$ haloalkyl, amino, $C_1$-$C_6$ alkylamino, di-($C_1$-$C_6$ alkyl)amino, amino-$C_1$-$C_6$ alkyl, $C_1$-$C_6$ alkylamino-$C_1$-$C_6$ alkyl, or di-($C_1$-$C_6$ alkyl)amino-$C_1$-$C_6$ alkyl.

2. The compound of claim 1, wherein the compound is formula (Ia):

(Ia)

3. The compound of claim 1, wherein the compound is formula (Ib):

(Ib)

4. The compound of claim 1, wherein subscript n is 0.

5. The compound of claim 1, wherein $R^{3a}$ and $R^{3b}$ are each hydrogen.

6. The compound of claim 1, wherein $R^2$ is halo.

7. The compound of claim 1, wherein $R^2$ is iodo.

8. The compound of claim 1, wherein $R^{2a}$ is halo.

9. The compound of claim 1, wherein $R^{2a}$ is fluoro.

10. The compound of claim 1, wherein
$R^1$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl) amino-$C_1$-$C_6$ alkyl, or heterocycloalkyl-$C_1$-$C_6$ alkyl, wherein each of the $C_3$-$C_8$ cycloalkyl and heterocycloalkyl groups is unsubstituted or substituted with one to six $R^6$ and each $R^6$ is independently hydroxy or $C_1$-$C_6$ alkyl; or
$R^1$ is $R^5$—C(O)—$C_1$-$C_6$ alkyl and $R^5$ is hydroxy, $C_1$-$C_6$ alkoxy, amino, or hydroxyamino.

11. The compound of claim 1, wherein $R^1$ is $C_1$-$C_6$ hydroxyalkyl.

12. The compound of claim 1, wherein $R^1$ is —OR$^4$ and $R^4$ is hydrogen, $C_1$-$C_6$ alkyl, $C_3$-$C_8$ cycloalkyl, $C_3$-$C_8$ cycloalkyl-$C_1$-$C_6$ alkyl, $C_1$-$C_6$ hydroxyalkyl, $C_1$-$C_6$ alkoxy-$C_1$-$C_6$ alkyl, amino-$C_1$-$C_6$ alkyl, $C_1$-$C_6$ alkylamino-$C_1$-$C_6$ alkyl, di-($C_1$-$C_6$ alkyl) amino-$C_1$-$C_6$ alkyl, heterocycloalkyl, or heterocycloalkyl-$C_1$-$C_6$ alkyl, wherein each of the $C_3$-$C_8$ cycloalkyl and heterocycloalkyl groups is unsubstituted or substituted with one to six $R^6$ and each $R^6$ is independently hydroxy or $C_1$-$C_6$ alkyl.

13. The compound of claim 1, wherein $R^1$ is —OR$^4$ and $R^4$ is $C_1$-$C_6$ hydroxyalkyl.

14. The compound of claim 1, wherein $R^1$ is selected from the group consisting of hydrogen, —OH,

15. The compound of claim 1, selected from the group consisting of:

-continued or a stereoisomer, mixture of stereoisomers, or a pharmaceutically acceptable salt thereof.

16. A pharmaceutical composition comprising a compound of claim 1 and a pharmaceutically acceptable carrier.

17. A method of treating a MEK-inhibitor responsive dermal disorder in a patient in need thereof, comprising administering a therapeutically effective amount of a compound of claim 1, or a stereoisomer, mixture of stereoisomers, or a pharmaceutically acceptable salt thereof, to the patient.

18. The method of claim 17, wherein the MEK-inhibitor responsive dermal disorder is selected from the group consisting of dermal rasopathy, neurofibromatosis type 1, dermal neurofibroma, subdermal neurofibroma, and superficial plexiform neurofibroma.

19. The method of claim 18, wherein the dermal rasopathy is selected from the group consisting of psoriasis, keratocanthoma (KA), hyperkeratosis, papilloma, Noonan syndrome (NS), cardiofaciocutaneous syndrome (CFC), Costello syndrome (faciocutaneoskeletal syndrome or FCS syndrome), oculoectodermal syndrome, cafe au lait spots, and Multiple lentigines syndrome (formerly called Leopard syndrome).

20. The method of claim 17, wherein the compound is administered topically, transdermally, or intralesionally.

21. The compound of claim 1, wherein the compound is:

or a pharmaceutically acceptable salt thereof.

22. The compound of claim 1, wherein the compound is:

or a pharmaceutically acceptable salt thereof.

23. The compound of claim 1, wherein the compound is:

or a pharmaceutically acceptable salt thereof.

24. The compound of claim 1, wherein the compound is:

or a pharmaceutically acceptable salt thereof.

* * * * *